US006936700B2

(12) United States Patent
Kasina

(10) Patent No.: US 6,936,700 B2
(45) Date of Patent: Aug. 30, 2005

(54) BRIDGED AROMATIC SUBSTITUTED AMINE LIGANDS WITH DONOR ATOMS

(75) Inventor: Sudhakar Kasina, Mercer Island, WA (US)

(73) Assignee: NeoRx Corporation, Seattle, WA (US)

(*) Notice: Subject to any disclaimer, the term of this patent is extended or adjusted under 35 U.S.C. 154(b) by 0 days.

(21) Appl. No.: 10/346,311

(22) Filed: Jan. 17, 2003

(65) Prior Publication Data
US 2003/0158393 A1 Aug. 21, 2003

Related U.S. Application Data

(60) Continuation of application No. 09/724,834, filed on Nov. 28, 2000, now Pat. No. 6,528,627, which is a continuation of application No. 09/310,455, filed on May 12, 1999, now Pat. No. 6,187,910, which is a division of application No. 08/829,533, filed on Mar. 28, 1997, now Pat. No. 6,005,083.

(51) Int. Cl.$^7$ ............................................. C07F 5/00
(52) U.S. Cl. ........................... 534/10; 534/14; 534/15; 424/1.65; 540/450; 540/470; 540/467
(58) Field of Search .......................... 424/1.11, 1.65; 534/10–16; 564/188, 306; 544/242, 296, 297, 298, 334, 327, 322; 546/255, 261; 568/61, 67; 548/303.7; 549/22, 37, 60, 28; 556/221, 231, 77, 116, 107, 137; 540/450, 465, 467, 470

(56) References Cited

U.S. PATENT DOCUMENTS

| 2,977,279 A | 3/1961 | Kosmiu et al. ............... 167/22 |
| 3,027,391 A | 3/1962 | Frigerio et al. ........... 260/429.1 |
| 4,293,537 A | 10/1981 | Wong ............................ 424/1 |
| 4,421,735 A | 12/1983 | Haber et al. ................. 424/1.1 |
| 4,452,774 A | 6/1984 | Jones et al. .................. 424/1.1 |
| 4,515,767 A | 5/1985 | Simón et al. ................. 424/1.1 |
| 4,560,548 A | 12/1985 | Simon et al. ................. 424/1.1 |
| 4,673,562 A | 6/1987 | Davison et al. .............. 424/1.1 |
| 4,722,892 A | 2/1988 | Meares et al. .................. 435/7 |
| 4,732,974 A | 3/1988 | Nicolotti et al. ............. 530/390 |
| 4,746,505 A | 5/1988 | Jones et al. .................. 424/1.1 |
| 4,758,682 A | 7/1988 | Collins et al. ............... 556/137 |
| 4,789,736 A | 12/1988 | Canning et al. ............... 534/14 |
| 4,818,813 A | 4/1989 | Nowotnik et al. ............. 534/14 |
| 4,831,122 A | 5/1989 | Buchsbaum et al. ......... 530/389 |
| 4,853,209 A | 8/1989 | Kaplan ........................ 424/1.1 |
| 4,861,869 A | 8/1989 | Nicolotti et al. ............. 530/402 |
| 4,863,713 A | 9/1989 | Goodwin et al. ............. 424/1.1 |
| 4,897,254 A | 1/1990 | Simon et al. ................. 424/1.1 |
| 4,897,255 A | 1/1990 | Fritzberg et al. ............. 424/1.1 |
| 4,898,724 A | 2/1990 | Simon et al. ................. 424/1.1 |
| 4,925,650 A | 5/1990 | Nosco et al. ................. 424/1.1 |
| 4,933,456 A | 6/1990 | Rocklage et al. ............... 546/5 |
| 4,959,304 A | 9/1990 | Simonson ...................... 435/7 |
| 4,963,682 A | 10/1990 | Bodor ........................ 546/338 |
| 4,963,688 A | 10/1990 | Bodor ........................ 546/316 |
| 4,976,950 A | 12/1990 | Simon et al. ................. 424/1.1 |
| 4,987,227 A | 1/1991 | Burrows et al. ............. 540/452 |
| 5,002,754 A | 3/1991 | Deutsch ....................... 424/1.1 |
| 5,019,497 A | 5/1991 | Olsson ....................... 435/7.23 |
| 5,021,571 A | 6/1991 | Mease et al. ................ 544/166 |
| 5,026,913 A | 6/1991 | McBride et al. ............. 564/440 |
| 5,032,678 A | 7/1991 | Washino et al. ............... 534/14 |
| 5,037,630 A | 8/1991 | Fritzberg et al. ............. 424/1.1 |
| 5,053,503 A | 10/1991 | Dean et al. .................. 540/474 |
| 5,057,301 A | 10/1991 | Wilbur et al. ................ 424/1.1 |
| 5,059,412 A | 10/1991 | Simon et al. ................. 424/1.1 |
| 5,059,541 A | 10/1991 | Fritzberg et al. ............. 436/501 |
| 5,061,641 A | 10/1991 | Shochat et al. .............. 436/545 |
| 5,064,633 A | 11/1991 | Simon et al. ................. 424/1.1 |
| 5,066,478 A | 11/1991 | Simon et al. ................. 424/1.1 |
| 5,071,965 A | 12/1991 | Dunn et al. ................... 534/14 |
| 5,075,099 A | 12/1991 | Srinivasan et al. .......... 424/1.1 |
| 5,079,346 A | 1/1992 | Kung .......................... 534/10 |
| 5,080,884 A | 1/1992 | McBride et al. ............. 424/1.1 |
| 5,089,249 A | 2/1992 | Fritzberg et al. ............. 424/1.1 |
| 5,091,514 A | 2/1992 | Fritzberg et al. .............. 534/14 |
| 5,104,638 A | 4/1992 | Nosco ........................ 424/1.1 |
| 5,106,951 A | 4/1992 | Morgan, Jr. et al. ....... 530/391.9 |
| 5,112,594 A | 5/1992 | Woulfe et al. ............... 424/1.1 |
| 5,112,595 A | 5/1992 | Woulfe et al. ............... 424/1.1 |
| 5,112,953 A | 5/1992 | Gustavson ................. 530/391.5 |
| 5,112,954 A | 5/1992 | Abrams et al. ............ 530/391.9 |
| 5,120,526 A | 6/1992 | Fritzberg et al. ............. 424/1.1 |
| 5,133,956 A | 7/1992 | Garlich et al. ............... 424/1.1 |
| 5,164,176 A | 11/1992 | Gustavson et al. .......... 424/1.1 |
| 5,167,948 A | 12/1992 | Wenzel ....................... 424/1.1 |
| 5,169,933 A | 12/1992 | Anderson et al. .......... 530/391.3 |
| 5,175,257 A | 12/1992 | Kasina et al. ............. 530/391.5 |
| 5,175,343 A | 12/1992 | Fritzberg et al. .............. 534/14 |
| 5,220,000 A | 6/1993 | Theodoropulos ............ 424/1.1 |
| 5,225,181 A | 7/1993 | Srivastava et al. .......... 560/145 |

(Continued)

FOREIGN PATENT DOCUMENTS

| DE | 26 06 721 A1 | 9/1976 |
| DE | 26 16 984 A1 | 10/1977 |
| DE | 32 28 503 A1 | 2/1984 |
| EP | 001 812 A1 | 5/1979 |
| EP | 038 546 B1 | 10/1981 |

(Continued)

OTHER PUBLICATIONS

Ahmad et al., Chem. Abstract 118: 159789, 1993.
Atkins et al., "Biodistribution of Sn–117m(4+)DTPA for Palliative Therapy of Painful Osseous Metastases," Radiology 286: 279–283, 1993.

(Continued)

Primary Examiner—Dameron Jones
(74) Attorney, Agent, or Firm—Schwegman, Lundberg, Woessner & Kluth, P.A.

(57) ABSTRACT

The present invention provides for substituted metal chelating compounds in which at least two of the chelating atoms are nitrogen which are directly attached to aromatic rings and one or more of those nitrogen atoms has attached thereto a substituent other than hydrogen, and methods for making and using these compounds.

13 Claims, No Drawings

U.S. PATENT DOCUMENTS

| | | | |
|---|---|---|---|
| 5,242,679 A | 9/1993 | Fritzberg et al. | 424/1.1 |
| 5,243,073 A | 9/1993 | Neumann et al. | 564/15 |
| 5,250,666 A | 10/1993 | Gustavson et al. | 530/391.5 |
| 5,252,713 A | 10/1993 | Morgan, Jr. et al. | 530/391.7 |
| 5,271,927 A | 12/1993 | Parker et al. | 424/9 |
| 5,279,811 A | 1/1994 | Bergstein et al. | 424/1.1 |
| 5,286,848 A | 2/1994 | Honzawa | 530/363 |
| 5,302,370 A | 4/1994 | Neumeier et al. | 424/1.53 |
| 5,310,536 A | 5/1994 | Srinivasan | 424/1.65 |
| 5,319,143 A | 6/1994 | Messersmith et al. | 564/500 |
| 5,322,678 A | 6/1994 | Morgan, Jr. et al. | 424/1.53 |
| 5,324,502 A | 6/1994 | Green et al. | 424/1.81 |
| 5,330,737 A | 7/1994 | Rajagopalan | 424/1.65 |
| 5,330,738 A | 7/1994 | Nosco | 424/1.65 |
| 5,334,729 A | 8/1994 | Mease et al. | 548/546 |
| 5,362,475 A | 11/1994 | Gries et al. | 424/9 |
| 5,371,184 A | 12/1994 | Rajagopalan et al. | 530/324 |
| 5,373,093 A | 12/1994 | Vallarino et al. | 534/15 |
| 5,382,654 A | 1/1995 | Lyle et al. | 530/311 |
| 5,476,644 A | 12/1995 | Illig et al. | 424/1.11 |
| 5,508,458 A | 4/1996 | Zhao | 556/45 |
| 5,648,063 A | 7/1997 | Gries et al. | 424/9.363 |
| 5,676,928 A | 10/1997 | Klaveness et al. | 424/9.321 |
| 6,005,083 A * | 12/1999 | Kasina | 534/10 |
| 6,024,937 A * | 2/2000 | Kasina et al. | 424/1.65 |
| 6,177,551 B1 * | 1/2001 | Kasina | 534/10 |
| 6,187,910 B1 * | 2/2001 | Kasina | 534/10 |
| 6,528,627 B1 * | 3/2003 | Kasina | 534/10 |
| 2003/0158393 A1 * | 8/2003 | Kasina | 534/11 |

FOREIGN PATENT DOCUMENTS

| | | |
|---|---|---|
| EP | 055 028 A1 | 6/1982 |
| EP | 123 307 A2 | 10/1984 |
| EP | 163 294 A2 | 12/1985 |
| EP | 200 211 A1 | 11/1986 |
| EP | 237 150 A2 | 9/1987 |
| EP | 317 873 A1 | 5/1989 |
| EP | 432 988 A1 | 6/1991 |
| EP | 603 403 A1 | 6/1994 |
| JP | 56-7725 | 1/1981 |
| WO | WO 91/17168 | 11/1991 |
| WO | WO 92/07860 | 5/1992 |
| WO | WO 93/15770 | 8/1993 |
| WO | WO 94/08949 | 4/1994 |
| WO | WO 94/26754 | 11/1994 |
| WO | WO 95/32192 | 11/1995 |
| WO | WO 97/01360 | 1/1997 |

OTHER PUBLICATIONS

Blankenberg et al., "Increased Localization Of TC–99m Hydrazino Nicotinamide (Hynic) Labeled Annexin V Lipocortin In Lymphatic Tissue Of Animals Treated With Dexamethasone," *Journal of Nuclear Medicine* 38(5 Suppl.): p. 268P–269P, Abstract No. 1132, 1997.

Bryson et al., "Protecting Groups in the Preparation of Thiolate Complexes of Technetium," *Inorganic Chemistry* 29(16): 2948–2951, 1990.

Cheesman et al., "Technetium–99m ECD: Ester–Derivatized Diamine–Dithiol Tc Complexes for imaging brain perfusion," *Journal of Nuclear Medicine* 29(5 Suppl.): p. 788, Abstract No. 197, 1988.

De Ligny et al., "Investigation of Two New [$^{99m}$Tc] Tc–HEDP Preparations That Can be Expected to Give a Better Lesion–to–normal–bone Uptake Ratio When Used as Bone Scanning Agents," *Nucl. Med. Biol.* 20(1): 23–29, 1993.

Dewanjee, "Localization of $^{113m}$In– and $^{67}$Ga–Labeled Poly–methylene–Phosphonates in Myocardial Infarct," *Nuclear Medicine* 16(4): 151–156, 1977.

Dowerah et al., *Chem. Abstract 107:* 125851, 1987.

Francesconi et al., "Technetium–99m N,N'–Bis(2–mercapto–2–methylproply)–2–aminobenzylamine: Technetium–99m Complexes of a Novel Bis (aminoethanethiol) Ligand," *J. Med. Chem.* 37(20): 3282–3288, 1994.

Francini et al., "Treatment of Bone Metastases with Dichloromethylene Bisphonate," *Journal of Clinical Oncology* 10(4): 591–598, 1992.

Fujisawa et al., "Critical Current Densities in Superconducting Y–Ba–Cu–O Prepared by Chelating Method," *Japanese Journal of Applied Physics* 29(10): 1914–1917, 1990.

Goeckeler et al., "Analysis of Urine Samples from Metastatic Bone Cancer Patients Administered $^{153}$Sm–EDTMP," *Nucl. Med. Biol.* 20(5): 657–661, 1993.

Goeckeler et al., "Skeletal Localization of Samarium–153 Chelates: Potential Therapeutic Bone Agents," *J. Nucl. Med.* 28(4): 495–504, 1987.

Gürsu et al., "The Reaction of N–Chloroacetylbenzamide with Some Aromatic Amines and Synthesis of Some Quarternary Pyridinium Compounds," *J. Fac. Pharm. Instanbul* 17: 119–134, 1981.

"Indium–111," Reynolds (ed.), *Martindale—The Extra Pharmacopoeia*, 31$^{st}$ Edition, Royal Pharmaceutical Society, London, GB, 1996, p. 1465, paragraph 5860–g.

Ingold et al., "Mechanisms of, and Constitutional Factors Controlling, the Hydrolysis of Carboxylic Esters. Part VIII. Energies Associated with Induced Polar Effects in the Hydrolysis of Substituted Benzoic Esters," *J. Chem. Soc.:* 222–225, 1935.

Jaffé, "A Reexamination of the Hammett Equation," *Chem. Rev.;* 191–261, 1953.

Kasina et al., "Preformed Chelate TC–99m Radiolabeling Of r–Annexin V For Arterial Thrombus Imaging," *Journal of Nuclear Medicine* 37(5 Suppl.): p. 29P, Abstract No. 106, 1996.

Láznícek et al., "Comparison of Biological Characteristics of EDTMP Complexes with $^{99m}$Tc, $^{111}$In and $^{153}$Sm in Rats," *Appl. Radiat. Isot.* 45(9): 949–953, 1994.

Léveillé et al., "Intrasubject Comparison Between Technetium–99m–ECD and Technetium 99m–HMPAO in Healthy Human Subjects," *J. Nucl. Med.* 33(4): 480–484, 1992.

Lever et al., "Pulmonary Accumulation of Neutral Diamine Dithiol Complexes of Technetium–99m," *Journal of Pharmaceutical Sciences* 83(6): 802–809, 1994.

Louw et al., "Evaluation of Samarium–153 and Holmium–166–EDTMP in the Normal Baboon Model," *Nuclear Medicine & Biology* 23(8): 935–940, 1996.

Mastrostamatis et al., "Tridentate Ligands Containing the SNS Donor Atom Set as a Novel Backbone for the Development of Technetium Brain–Imaging Agents," *J. Med. Chem.* 37(20): 3212–3218, 1994.

Matsuda et al., "Comparative SPECT Study of Stroke Using Tc–99m ECD, I–123 IMP, and Tc–99m HMPAO," *Clinical Nuclear Medicine* 16(9): 754–758, 1993.

Mertens et al., "Strontium–89 and Low–Dose Infusion Cisplatin for Patients with Hormone Refractory Prostate Carcinoma Metastatic to Bone: A Preliminary Report," *J. Nucl. Med.* 33(8): 1437–1443, 1992.

Milligan et al., "Colorimetric Determination of Calcium Using Reagents of the Glyoxal Bis(2–Hydroxyanil) Class," *Analytical Chemistry* 44(11): 1822–1829, 1972.

Neves et al., "Neutral Technetium(II)–99m Complexes as Potential Brain Perfusion Imaging Agents," *Nucl. Med. Biol.* 14(5): 503–510, 1987.

Orlandi et al., "Regional Cerebral Blood Flow and Distribution of [$^{99m}$Tc] Ethyl Cysteinate Dimer in Nonhuman Primates," *Stoke* 21(7): 1059–1063, 1990.

Papadopoulos et al., "$^{99m}$Tc–DADT Complexes Substituted With Heterocyclic Amines: Effect of Substitution on In Vivo Reactivity," *Nuclear Medicine and Biology* 20(1): 105–115, 1993.

Rajagopalan et al., "Preparation, Characterization, and Biological Evaluation of Technetium(V) and Rhenium(V) Complexes of Novel Heterocyclic Tetradendate N₃S Ligands," *Bioconjugate Chem.* 8(3): 407415, 1997.

Renn et al., "New approaches to delivering metal–labeled antibodies to tumors: Synthesis and characterization of new biotinyl chelate conjugates for pre–targeted diagnosis and therapy," *Journal of Controlled Release 39:* 239–249, 1996.

"Rhenium–186," Reynolds (ed.), *Martindale—The Extra Pharmacopoeia, 31st Edition,* Royal Pharmaceutical Society, London, GB, 1996, pp. 1467–1468, paragraph 3879–n.

"Samarium–153," Reynolds (ed.), *Martindale—The Extra Pharmacopoeia, 31st Edition,* Royal Pharmaceutical Society, London, GB, 1996, pp. 1467–1468, paragraph 12226–a.

Schomäcker et al., "Influence of Extratumoral Organ Activities of Tumor–Affine Samarium–153–Preparations," *Nuklearmedizin* 36(2): 47–51, 1997.

Schomäcker et al., "The Effect of EDTMP on the Biodistribution of Tumour–Affine Radionuclides," *Nuklear Medizin* 32(1): 23–26, 1993.

Stahl et al., "$^{99m}$Technetium Labelling Of Antibodies Using Methylphosphonylated, Bifunctional Cyclams As Chelators," *Bioorganic & Medicinal Chemistry Letters* 4 (21): 2597–2600, 1994.

Stratton et al., "Selective Uptake of Radiolabeled Annexin V on Acute Porcine Left Atrial Thrombi," *Circulation* 92(10): 3113–3121, 1995.

Subramanian and Wolf, "A New Radiochemical Method to Determine the Stability Constants of Metal Chelates Attached to a Protein," *The Journal of Nuclear Medicine* 31(4): 480–488, 1990.

Subramanian et al., "Indium–113m–Labeled Polyfunctional Phosphonates As Bone–Imaging Agents," *Journal of Nuclear Medicine* 16(11): 1080–1084, 1975.

Sun et al., "Targeting Radiopharmaceuticals–II. Evaluation of New Trivalent Metal Complexes With Different Overall Charges," *International Journal Of Radiation Applications And Instrumentation Part B: Nuclear Medicine Biology* 18(3): 323–330, 1991.

Taylor et al., "Technetium–99m–N1–(2–Mercapto–2–Methylpropyl)–N2–(2–Propargylthio–2–Methylpropyl)–1,2–Benzenediamine (T691): Preclinical Studies of a Potential New Tracer of Regional Cerebral Perfusion," *J. Nucl. Med.* 33(10): 1836–1842, 1992.

"Technetium," Budavari et al. (eds.), *The Merck Index, An Encyclopedia Of Chemicals, Drugs, And Biologicals,* Merck & Co., Inc., Whitehouse Station, US, p. 1556, paragraph 9256.

"Technetium–99m," Reynolds (ed.), *Martindale—The Extra Pharmacopoeia,* 31st *Edition,* Royal Pharmaceutical Society, London, GB, 1996, pp. 1467–1468, paragraph 5878–c.

Teclothiazide, Budavari et al. (eds.), *The Merck Index, An Encyclopedia Of Chemicals, Drugs, And Biologicals,* Merck & Co., Inc., Whitehouse Station, US, p. 1557, paragraph 9261.

Tedjamulia et al., "Evaluation of the Brain–Specific Delivery of Radioiodinated (Iocophenyl)alkyl–Substituted Amines Coupled to a Dihydropyridine Carrier," *J. Med. Chem.* 28: 1674–1680, 1995.

Tsien, "New Calcium Indicators and Buffers with High Selectivity against Magnesium and Protons: Design, Synthesis, and Properties of Prototype Structures," *Biochemistry* 19(11): 2396–2404, 1980.

Vallabhajosula et al., "Technetium–99m ECD: A New Brain Imaging Agent: In Vivo Kinetics and Biodistribution Studies in Normal Human Subjects," *J. Nucl. Med.* 30(5): 599–604, 1989.

Vaughan et al., *Chem. Abstract* 114: 54730, 1991.

Volkert et al., "In Vivo Skeletal Localization Properties of $^{99m}$Tc Complexes of Large Phosphonate Ligands," *International Journal of Radiation Applications and Instrumentation Part B: Nuclear Medicine and Biology* 13(1): 31–37, 1986.

Volkert et al., "Skeletal Uptake Properties Of Tc–99m–Labeled Multidentate Phosphonate Ligands," *Journal of Labelled Compounds and Radiopharmaceuticals* 21(11–12): 1063–1065, 1984.

Volkert et al., "Therapeutic Radionuclides: Production and Decay Property Considerations," *J. Nucl. Med.* 32(1): 174–185, 1991.

Wu et al., "Investigations of N–linked Macrocycles for $^{111}$In and [90]Y Labeling of Proteins," *Nuclear Medicine and Biology* 19(2): 239–244, 1992.

"Yttrium–90," Reynolds (ed.), *Martindale—The Extra Pharmacopoeia, 31st Edition,* Royal Pharmaceutical Society, London, GB, 1996, pp. 1467–1468, paragraph 5883–y.

* cited by examiner

BRIDGED AROMATIC SUBSTITUTED AMINE LIGANDS WITH DONOR ATOMS

CROSS-REFERENCE TO RELATED APPLICATIONS

This application is a continuation of U.S. patent application Ser. No. 09/724,834, filed Nov. 28, 2000, now U.S. Pat. No. 6,528,627; which application is a continuation of U.S. patent application Ser. No. 09/310,455, filed May 12, 1999, which issued as U.S Pat. No. 6,187,910; which application is a divisional of U.S. patent application Ser. No. 08/829,533, filed Mar. 28, 1997, which issued as U.S. Pat. No. 6,005,083; all of which applications are incorporated by reference herewith in their entirety.

TECHNICAL FIELD

The present invention relates generally to chelation compounds, radionuclide metal chelate compounds (i.e., complexes) and radiolabeled targeting moieties (i.e., conjugates) formed therefrom, and methods of making and using these compounds, complexes and conjugates for diagnostic and therapeutic purposes. This invention is more particularly related to compounds in which at least two of the chelating atoms are nitrogen atoms which are directly attached to aromatic rings and there is a non-hydrogen substituent directly attached to at least one of these nitrogen chelating atoms.

BACKGROUND OF THE INVENTION

Radiolabeled chelation compounds have been studied and used as pharmaceuticals for diagnostic and therapeutic purposes for a number of years. The requirements for a useful radiolabeled chelating compound are well known to those skilled in the art of nuclear medicine and radiopharmaceutical research. Briefly, these requirements include: efficient final preparation of the radiopharmaceutical, such that preparation in the hospital or pharmacy is possible; efficient transport of the radiopharmaceutical to the target organ; efficient extraction of the radiopharmaceutical by the target organ, such that adequate target to background ratios are achieved to allow diagnostic and therapeutic distinctions; and adequate retention in the target organ to allow detection and therapy using conventionally available radiation monitoring equipment. Representative organs of interest are those containing malignant cells or activated platelets. Imaging agents and therapeutic agents have typically been unsuitable due to poor in vivo stability post-chelation, resulting in inadequate retention and accretion by the effected cells.

Thus, there is a need in the art for improved chelation compounds for imaging and therapy. The present invention fulfills this need and further provides other related advantages.

SUMMARY OF THE INVENTION

Briefly stated, the present invention in one aspect provides compounds having the formula:

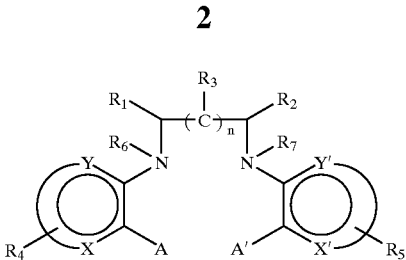

wherein:
  n=0 or 1;
  $R_1$ and $R_2$ are independently selected from hydrogen, =O, with the proviso that both are not =O, —$(CH_2)_m$-Z where m is 0–10 and Z represents a conjugation group or targeting moiety, and —$(Ch_2)_m$—W where m is 0–10 and W represents a hydrolyzable group, or $R_1$ and $R_2$ are taken together to form a cyclic anhydride or a benzene ring;
  $R_3$ is hydrogen, lower alkyl, alkoxy, halogen, hydroxyl, nitro, —$(CH_2)_m$-Z or —$(CH_2)_m$—W;
  $R_4$ and $R_5$ are attached at one or more of the ring positions and are independently selected from hydrogen, lower alkyl, alkoxy, halogen, hydroxyl, nitro, —$(CH_2)_m$-Z and —$(CH_2)_m$—W;
  $R_6$ and $R_7$ are independently selected from hydrogen with the proviso that both are not hydrogen, lower alkyl, alkoxy, halogen, hydroxyl, nitro, —$(CH_2)_m$-Z, —$(CH_2)_m$—W and

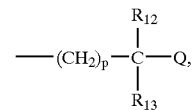

where Q represents a multivalent acid functionality group able to coordinate with metal ions, and p=0 to 1; $R_{12}$ and $R_{13}$ are independently selected from hydrogen, hydroxyl, carboxyl, phosphonic and hydrocarbon radicals having from 1–10 carbon atoms, and physiologically acceptable salts of the acid radicals;
  X, X', Y and Y' are independently selected from carbon, nitrogen, oxygen and sulfur to independently form five or six member aromatic rings wherein the remaining ring atoms are carbon;
  A and A' are independently selected from sulfur, nitrogen and oxygen, where sulfur may bear a hydrogen or a sulfur protecting group, or where A and A' are both sulfur, A and A' may be joined together by a bond; where an oxygen or a nitrogen may bear a hydrogen; or where A or A' is nitrogen, A may bear $R_8$ or $R_{10}$ or both and A' may bear $R_9$ or $R_{11}$ or both, wherein $R_8$, $R_9$, $R_{10}$ and $R_{11}$ are independently selected from lower alkyl, alkoxy, halogen, hydroxyl, nitro, —$(CH_2)_m$-Z, —$(CH_2)_m$—W and

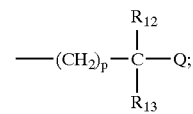

or $R_8$ and $R_{10}$ may be joined to form a cyclic anhydride or $R_9$ and $R_{11}$ may be joined to form a cyclic anhydride; or when A and A' are both nitrogen, $R_{10}$ and $R_{11}$ may be joined to form T, where T is

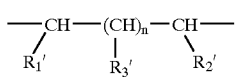

and n is 0 to 1, and $R_1'$ and $R_2'$ are independently selected from hydrogen, =O, with the proviso that both are not =O, —$(CH_2)_m$-Z and —$(CH_2)_m$—W or $R_1'$ and $R_2'$ are taken together to form a cyclic anhydride or a benzene ring; and $R_3'$ is hydrogen, lower alkyl, alkoxy, halogen, hydroxyl, nitro, —$(CH_2)_m$-Z and —$(CH_2)_m$—W; and said compound has at least one Z, W and Q.

In another aspect, the invention provides chelates comprising radionuclide metals (including oxides or nitrides thereof) complexed by a compound described above A preferred metal chelate compound is of the formula:

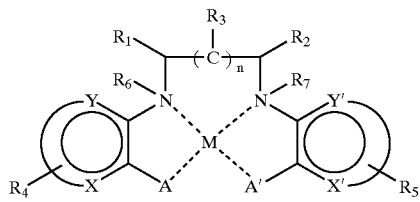

wherein:

M is a radionuclide metal or an oxide or a nitride thereof selected from technetium, copper, rhenium, sumarian, yttrium, indium, lead, bismuth, ruthenium, rhodium, gold and palladium;

n=0 or 1;

$R_1$ and $R_2$ are independently selected from hydrogen, =O with the proviso that both are not =O, —$(CH_2)_m$-Z where m is 0–10 and Z represents a conjugation group or targeting moiety, and —$(CH_2)_m$—W where m is 0–10 and W represents a hydrolyzable group, or $R_1$ and $R_2$ are taken together to form a cyclic anhydride or a benzene ring;

$R_3$ is hydrogen, lower alkyl, alkoxy, halogen, hydroxyl, nitro, —$(CH_2)_m$-Z or —$(CH_2)_m$—W;

$R_4$ and $R_5$ are attached at one or more of the ring positions and are independently selected from hydrogen, lower alkyl, alkoxy, halogen, hydroxyl, nitro, —$(CH_2)_m$-Z and —$(CH_2)_m$—W;

$R_6$ and $R_7$ are independently selected from hydrogen with the proviso that both are not hydrogen, lower alkyl, alkoxy, halogen, hydroxyl, nitro, —$(CH_2)_m$-Z, —$(CH_2)_m$—W— and

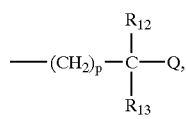

where Q represents a multivalent acid functionality group able to coordinate with metal ions, and p=0 to 1; $R_{12}$ and $R_{13}$ are independently selected from hydrogen, hydroxyl, carboxyl, phosphonic and hydrocarbon radicals having from 1–10 carbon atoms, and physiologically acceptable salts of the acid radicals;

X, X', Y and Y' are independently selected from carbon, nitrogen, oxygen and sulfur to independently form 5 or 6 member aromatic rings wherein the remaining ring atoms are carbon;

A and A' are independently selected from sulfur, nitrogen and oxygen, where A or A' is nitrogen, A may bear $R_8$ or $R_{10}$ or both and A' may bear $R_9$ or $R_{11}$ or both, wherein $R_8$, $R_9$, $R_{10}$ and $R_{11}$ are independently selected from lower alkyl, alkoxy, halogen, hydroxyl, nitro, —$(CH_2)_m$-Z, —$(CH_2)_m$—W and

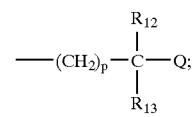

or $R_8$ and $R_{10}$ may be joined to form a cyclic anhydride or $R_9$ and $R_{11}$ may be joined to form a cyclic anhydride; or when A and A' are both nitrogen, $R_{10}$ and $R_{11}$ may be joined to form T, where T is

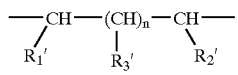

and n is 0 to 1, and $R_1'$ and $R_2'$ are independently selected from hydrogen, =O, with the proviso that both are not =O, —$(CH_2)_m$-Z or $R_1'$ and $R_2'$ are taken together to form a cyclic anhydride or a benzene ring; and $R_3'$ is hydrogen, lower alkyl, alkoxy, halogen, hydroxyl, nitro, —$(CH_2)_m$-Z or —$(CH_2)_m$—W; and said compound has at least one Z, W or Q.

Yet another aspect of the invention provides for the use of the chelation compounds described above in methods for diagnostic and therapeutic purposes. A diagnostic method is described for detecting the presence or absence of a target site within a mammalian host This method comprises providing to cells a diagnostically effective dose of a compound of the present invention which contains a metal radionuclide, such as $^{99m}TC$ and/or $^{111}In$, and detecting the biodistribution of the radionuclide. A therapeutic method is described for delivering a radionuclide, such as $^{186}Re/^{188}Re$, $^{90}Y$, and $^{153}Sm$, to a target site within a mammalian host. This method comprises providing to cells a therapeutically effective dose of a chelate compound of the present invention.

Other aspects of the invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

Targeting moiety—is any molecule that binds to a defined population of cells, and includes analogs of naturally occurring and synthetically or recombinantly prepared molecules. The targeting moiety may bind a receptor, an oligonucleotide, an enzymatic substrate, an antigenic determinant, or other binding site present on or in the target cell population. For example, a protein may be a targeting moiety. Antibodies and peptides are used throughout the specification as prototypical examples of targeting moieties. Tumor is used as a prototypical example of a target in describing the present invention.

Protein—as used herein, includes proteins, fusion proteins, polypeptides and peptides; and may be an intact molecule, a fragment thereof, or a functional equivalent thereof; and may be genetically engineered.

Antibody—as used herein, includes both polyclonal and monoclonal antibodies; and may be an intact molecule, a fragment thereof, or a functional equivalent thereof; and may be genetically engineered; examples of antibody fragments include F(ab')$_2$, Fab', Fab and Fv.

The present invention provides chelation compounds and radionuclide metal chelate compounds (i.e., complexes) prepared therefrom, as well as radiolabeled targeting moieties having the chelation compounds or chelates attached thereto (i.e., conjugates). The radionuclide metal chelates of the present invention may be attached to targeting moieties, such as antibodies and proteins, to form radiolabeled targeting moieties having diagnostic and therapeutic use Alternatively, the radionuclide metal chelates of the present invention may be used for diagnostic and therapeutic purposes without attachment to targeting moieties.

The present invention provides compounds that have a variety of uses, including for malignant cell imaging and therapy as well as thrombus imaging. The compounds are capable of rapidly complexing a metal as well as forming a stable metal chelate (complex). The presence of nitrogen atoms within the chelating compound accelerates complex formation with the metal. This acceleration is due in part to the fact that a metal (e.g., technetium) is a soft acid, and nitrogen (in the form of an amine or amide) is a base. Amines generally provide for a greater increase in chelation rates than amides Where sulfur atoms are additionally present within the chelating compound, they also provide for an increased rate of metal complexation and contribute to the stability of the resulting chelate The presence of phenolic hydroxyl groups within the chelating compound aid in faster kinetics of metal ion chelation The compounds of the present invention are characterized by desirable metal complex formation kinetic properties and desirable metal-chelate retention thermodynamic properties. The compounds of the present invention have the further advantage of nitrogen atoms attached directly to aromatic rings which aid in fast kinetics of chelation and further enhances the stability of the aromatic esters of this invention with respect to hydrolysis in the bloodstream. Furthermore, an additional advantage of the present invention is the presence of substituents attached to the nitrogen atoms within the chelating compound, which imparts a higher basicity to the chelation compound and allows for additional donor atoms for complexation, thereby expanding the type of radionuclides useful for radiotherapy and radiodetection in the present invention. In addition to the above advantages, the presence of substituents enhances pharmakokinetics and pharmacodynamics, such as the biopharmaceutical properties (i.e, absorption, distribution, metabolism and excretion).

The chelation compounds of the present invention have the following formula (I):

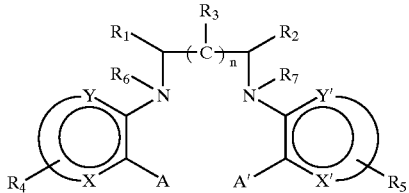

Examples of specific embodiments of the elements of the above formula include the following.

$R_1$ and $R_2$ may be independently selected from hydrogen (H); an oxy group (═O); —(CH$_2$)$_m$-Z where m is 0–10 and Z represents a conjugation group or targeting moiety; or —(CH$_2$)$_m$—W where m is 0–10 and W represents a hydrolyzable group. As used herein, the phrase independently selected means the selection of one substituent may be made without regard for the selection of any other substituent. Alternatively, $R_1$ and $R_2$ may be taken together to form a cyclic group, such as an anhydride or a benzene ring. As used herein, a benzene ring may be benzene or benzene with one or more substituents. A substituent may be any electron donating (methyl, methoxy, amino and the like) and/or electron withdrawing (halogens, nitro, carboxy, nitrile and the like) and functional groups (esters, imidates, carbaminates and the like) known in the art. Examples of such substituents include Cl, CH$_3$, OCH$_3$, F, Br, I, CF$_3$ and a triazene, such a —N═N—N (CH$_3$)$_2$.

As noted above, Z represents a conjugation group or a targeting moiety. A "conjugation group" in the compounds of the present invention is any chemically reactive group capable of forming a covalent bond with a targeting moiety under conditions that do not adversely affect the targeting moiety's functional properties. For example, where the targeting moiety is a protein such as an antibody, the conjugation group is sufficiently reactive with a functional group on the protein so that the reaction can be conducted in substantially aqueous solutions and does not have to be forced (e.g., by heating to high temperatures which may denature the protein).

A conjugation group may be strongly electrophilic or nucleophilic and thereby capable of reacting directly with a targeting moiety. A precursor to a conjugation group may be a weaker electrophile or nucleophile that requires activation prior to conjugation with a targeting moiety. Conversion of a group from a precursor group to a conjugation group is generally performed in a separate step prior to conjugation with a targeting moiety. However, where a targeting moiety is unreactive with the conversion reagents and unaffected by the reaction conditions, it is possible to generate a conjugation group in the presence of the targeting moiety.

An electrophilic conjugation group may react directly with a nucleophile, either through nucleophilic substitution or nucleophilic addition. In the present invention, electrophilic conjugation groups react with the targeting moiety acting as the nucleophile. A targeting moiety may naturally possess nucleophilic group(s). For example, a targeting moiety may contain an amino group or a sulfhydryl group. Alternatively, a targeting moiety may have been modified to contain nucleophilic group(s). Procedures for modifying molecules to contain nucleophilic groups are well known to those in the art (see, e.g., catalog of Pierce Chemical Co., Rockford, Ill., and U.S. Pat. No. 4,659,839).

Electrophilic groups which provide conjugation through nucleophilic substitution include those groups which contain substituents which are readily displaced. Such readily displaced substituents are commonly referred to as leaving groups. Leaving groups include halides which are readily displaced from alkyl halides and alphahalo carbonyl compounds, and carboxylate and stabilized oxyanions which are readily displaced from carbonyl-containing groups such as anhydrides and active esters, respectively. For example, in addition to halide ion leaving groups such as iodide, bromide, and chloride ions, other leaving groups include carboxylate ions such as acetate and trifluoroacetate and phenolate ions such as phenolate and p-nitrophenolate as well as tosylates and mesylates. Suitable active ester groups include N-hydroxysuccinimidyl, tetrafluorophenyl, nitrophenyl, and 1-hydroxybenzotriazolyl.

Electrophilic groups which provide conjugation through nucleophilic addition include those groups which contain unsaturated carbon atoms susceptible to nucleophilic addition. Suitable electrophilic carbon species include thiocyanates, isocyanates, isothiocyanates and maleimides.

As mentioned above, a conjugation group capable of reacting directly with a targeting moiety may be prepared by conversion of a weaker electrophilic or nucleophilic group to a stronger one. For example, a carboxylic acid group is a precursor group which may be activated, (e.g., by conversion into an active ester conjugation group capable of reaction with targeting moieties as described above). Another example of a conversion to a strong electrophilic group is deprotection of a phenylsulfonyl succinimide to provide a maleimide capable of reaction with nucleophilic targeting moieties as described above.

The conjugation group may also be a nucleophilic group, such as an amino or sulfhydryl group. Such a nucleophile is capable of reacting with an electrophilic targeting moiety, such as one that naturally possesses electrophilic group(s) or one that has been modified to include electrophilic group(s). For example, a targeting moiety may contain an active ester or a maleimide group. Alternatively, procedures for modifying molecules to contain electrophilic groups are well known to those in the art (see, e.g., catalog of Pierce Chemical Co., Rockford, Ill., and U.S. Pat. No. 4,671,958).

Alternatively, Z may be a targeting moiety rather than a conjugation group. A "targeting moiety" in the compounds of the present invention has the functional property that it binds to a defined target cell population, such as tumor cells. Preferred targeting moieties useful in this regard include proteins, peptides, antibody and antibody fragments, hormones, and vitamins such as biotin. Proteins corresponding to known cell surface receptors (including low density lipoproteins, transferrin and insulin), fibrinolytic enzymes, anti-HER2, platelet binding proteins such as annexins, avidin, streptavidin, and biological response modifiers (including interleukin, interferon, erythropoietin, colony-stimulating factor, TNF-tissue necrosis factors and similar cytokines) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs, including those of the above-listed targeting moieties, that retain the capacity to bind to a defined target cell population may also be used within the claimed invention. In addition, synthetic or recombinant targeting moieties may be designed and produced.

Functional equivalents of the aforementioned molecules are also useful as targeting moieties of the present invention. An example of a targeting moiety functional equivalent is a "mimetic" compound, which is an organic chemical construct designed to mimic the proper configuration and/or orientation for targeting moiety-target cell binding. Another example of a targeting moiety functional equivalent is a short polypeptide designated as a "minimal" polypeptide. Such a polypeptide is constructed using computer-assisted molecular modeling and mutants having altered binding affinity of the targeting moiety.

As disclosed above, preferred targeting moieties of the present invention are proteins, antibodies (polyclonal or monoclonal), peptides, oligonucleotides or the like. Polyclonal antibodies useful in the practice of the present invention are polyclonal (Vial and Callahan, *Univ. Mich. Med. Bull.* 20:284–6, 1956), affinity-purified polyclonal or fragments thereof (Chao et al., *Res. Comm. in Chem. Path. & Pharm.* (:749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species See, generally, Kohler and Milstein, *Nature* 256:495–97, 1975; *Eur. J. Immunol.* 6:511–19, 1976.

Human monoclonal antibodies or "humanized" murine antibody are also useful as targeting moieties in accordance with the present invention. For example, a murine monoclonal antibody may be "humanized" by genetically recombining the nucleotide sequence encoding the murine Fv region (i.e., containing the antigen binding sites) or the complementary determining regions ("CDR's") thereof with the nucleotide sequence encoding a human constant domain region and an Fc region (i.e., human framework), e.g., in a manner similar to that disclosed in U.S. Pat. Nos. 4,816,397, 4,816,567, 5,530,101 and 5,585,089. Some murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Another preferred targeting moiety of the present invention is an annexin and other platelet binding proteins, such as PAP-1 (Placental Anticoagulant Protein or Annexin V). Annexins are (with the exception of annexin II), single-chain, non-gylcosylated protein of approximately 36 kilodaltons. In the presence of calcium, these proteins have an especially high affinity for negatively-charged phospholipids, such as phosphatitylserine.

As mentioned above, W is a hydrolyzable group. As used herein, the term "hydrolyzable group" refers to any neutral organic group that provides a charged group upon hydrolysis. The hydrolysis may be chemical or enzymatic in nature. Examples of hydrolyzable groups include esters, imidates, and nitriles which may be hydrolyzed to carboxylic acids; and carbamates which may be hydrolyzed to amines.

Referring to the above formula, the distance by which the chelating nitrogen atoms are separated may be increased by interposing a methylene group, $—CH_2—$, between the carbon atoms bonded to the nitrogens depicted. When no methylene group is interposed, represented in the above formula where n=0, the chelating nitrogens are separated by two carbon atoms. When n=1, the interposed methylene group may be substituted with $R_3$.

$R_3$ may be hydrogen, a lower alkyl group, an alkyl group, an alkoxy group, a halogen, a hydroxyl group, a nitro group, $—(CH_2)_m-Z$ or $—(CH_2)_m—W$. As used throughout, a lower alkyl group is an alkyl group of hydrocarbon radicals having from 1–10 carbon atoms, and physiologically acceptable salts of the acid radicals which includes a substituted lower alkyl. A substituted lower alkyl group is a lower alkyl group that bears a halogen, perhaloalkyl, hydroxyl or alkoxy substituent; an alkoxy group is any alkoxy group of $C_6$ or less. Suitable halogens include fluorine, chlorine, bromine and iodine.

$R_4$ and $R_5$ may be attached at one or more of the aromatic ring positions, preferably the ring carbon atoms. $R_4$ and $R_5$ are independently selected from hydrogen, a lower alkyl group, an alkoxy group, a halogen, a hydroxyl group, a nitro group, $—(CH_2)_m\text{-}Z$ and $—(CH_2)_m—W$. For $R_4$ and $R_5$, preferred groups include lower alkyl groups such as methyl, alkoxy groups such as methoxy, and halogen groups such as fluorine. Preferred Z groups include active esters such as N-hydroxysuccinimide esters and maleimides. Preferred W groups include ester and carbamate groups, such as ethyl esters and ethyl carbamates. Preferably, such preferred alkyl groups, alkoxy groups, and ester groups are substituted at the aromatic ring carbon ortho or para to the chelating nitrogen depicted in formula I above.

$R_6$ and $R_7$ may be independently a hydrogen, lower alkyl, alkoxy, halogen, hydroxyl, nitro, $—(CH_2)_m\text{-}Z$, $—(CH_2)_m—W$ and

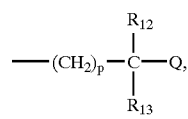

where Q represents a multivalent acid functionality capable of coordinating with metal ions, and p=0 to 1; $R_{12}$ and $R_{13}$ are independently selected from hydrogen, hydroxyl, carboxyl, phosphonic, and hydrocarbon radicals having from 1–10 carbon atoms, and physiologically acceptable salts of the acid radicals, and $R_{12}$ and $R_{13}$ may be the same as or different from one another. In one embodiment, $R_7$ may be hydrogen when $R_6$ is

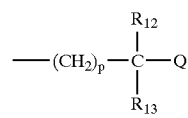

and Q is a phosphonic or a carboxylic acid and $R_6$ may be hydrogen when $R_7$ is

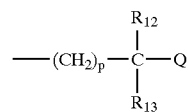

and Q is a phosphonic or a carboxylic acid, but $R_6$ and $R_7$ cannot both be hydrogen simultaneously. As noted above, Q represents a multivalent acid functionality. As used herein, the term multivalent acid functionality refers to any multivalent acid capable of coordinating a metal ion known to one of ordinary skill in the art. In preferred embodiments, $R_6$ or $R_7$ or both bear a Q containing substituent. Preferred multivalent acids are the following: a phosphonic acid, a carboxylic acid, a thioacetic acid and a sulfonic acid. Particularly preferred are a phosphonic acid and a carboxylic acid. The multivalent acid provides extra donor atoms which allow for binding of a metal through coordination of such donor atoms, thereby providing for a versatile chelation compound for diagnostic and therapeutic use.

The compounds of the present invention typically have one or more Q, Z and/or W groups. For example, a compound may have one Z or one W or one Q, or a combination of all three or some lesser combination. Alternatively, for example, a compound may have multiple Z and/or multiple W groups, and/or multiple Q groups.

A and A' may be independently selected from nitrogen, oxygen and sulfur. Where a sulfur is present, it may bear a hydrogen or a sulfur protecting group. Where A and A' are both sulfur, they may be joined together by a bond or any sulfur protecting group known in the art. Where an oxygen or a nitrogen is present, it may bear a hydrogen. Where A or A' is nitrogen, A may bear $R_8$ or $R_{10}$ or both and A' may bear $R_9$ or $R_{11}$ or both, wherein $R_8$, $R_9$, $R_{10}$ and $R_{11}$ are independently selected from a lower alkyl, alkoxy, halogen, hydroxyl, nitro, $—(CH_2)_m\text{-}Z$, $—(CH_2)_m—W$ and

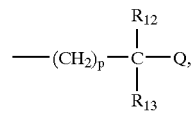

where Q represents a multivalent acid functionality capable of coordinating with metal ions, and p=0 to 1; $R_{12}$ and $R_{13}$ are independently selected from hydrogen, hydroxyl, carboxyl, phosphonic, and hydrocarbon radicals having from 1–10 carbon atoms, and physiologically acceptable salts of the acid radicals, and $R_{12}$ and $R_{13}$ may be the same as or different from one another; $R_8$ and $R_{10}$ may be joined to form a cyclic anhydride or $R_9$ and $R_{11}$ may be joined to form a cyclic anhydride. Where A and A' are both nitrogen, $R_{10}$ and $R_{11}$ may be joined to form T, where T is

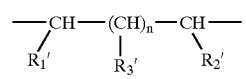

and n is 0 to 1. $R_1'$ and $R_2'$ may be independently selected from hydrogen, =O, $—(CH_2)_m\text{-}Z$ and $—(CH_2)_m—W$, or $R_1'$ and $R_2'$ are taken together to form a cyclic anhydride or a benzene ring. $R_3'$ is selected from hydrogen, lower alkyl, substituted lower, alkoxy, perhaloalkoxy, perhaloalkyl, halogen, hydroxyl, nitro, $—(CH_2)_m\text{-}Z$ and $—(CH_2)_m—W$ In a preferred embodiment where A and A' are both sulfur, the sulfur atoms are joined together by a bond thus forming a disulfide. In a preferred embodiment where A and A' are both nitrogen, $R_{10}$ and $R_{11}$ are joined to form T where n is either 0 or 1 and $R_8$ and $R_9$ are

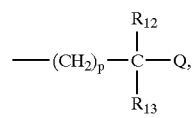

where Q represents multivalent acid functionality capable of coordinating with metal ions, and m=0 to 1; $R_{12}$ and $R_{13}$ are independently selected from hydrogen, hydroxyl, carboxyl, phosphonic, and hydrocarbon radicals having from 1–10 carbon atoms, and physiologically acceptable salts of the acid radicals, and $R_{12}$ and $R_{13}$ may be the same as or different from one another.

The chelation compounds of the present invention may be categorized by the number and type of chelating atoms (i.e. $N_xS_yO_z$ where x is 2 to 4, y is 0 to 2, and z is 0 to 2). For example, where both A and A' are nitrogen, the chelation compounds of the present invention are able to bind a metal through coordination with all four nitrogen atoms. Such a chelating compound may be referred to as an "$N_4$" ($N_4S_0O_0$) compound. In another embodiment, both A and A' are sulfur, resulting in the capacity for metal chelation through two nitrogen atoms and two sulfur atoms, and thus providing an "$N_2S_2$" ($N_2S_2O_0$) chelating compound. Alternatively, A may be nitrogen and A' may be sulfur or A may be sulfur and A' may be nitrogen. Either of these embodiments are capable of metal chelation involving three nitrogen atoms and a single sulfur atom, an "$N_3S$" ($N_3S_1O_0$) chelating compound. In another embodiment, A and/or A' may be oxygen atoms (e.g., hydroxyl groups). Where both A and A' are oxygen, an "$N_2O_2$" ($N_2S_0O_2$) chelating compound results. Other embodiments include "$N_3O$" ($N_3S_0O_1$) and "$N_2SO$" ($N_2S_1O_1$) chelation compounds where one of either A or A' is oxygen and the other is nitrogen or sulfur, respectively.

In a preferred embodiment of the present invention, the chelation compounds are able to bind a metal radionuclide with the donor atoms providing up to eight coordination sites For example, A and A' are both nitrogen, $R_{10}$ and $R_{11}$ may join the two nitrogen atoms, through the formation of T to create a cyclic "$N_4$" ($N_4S_0O_0$) chelation compound and wherein $R_6$, $R_7$, $R_8$ and $R_9$ may be

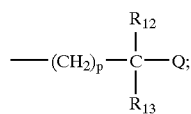

wherein Q is preferably a multivalent acid functionality, such as a phosphonic and/or a carboxylic acid. Thus, in addition to the four chelating atoms of nitrogen, the oxygen atoms of the multivalent acid functionality provide up to four additional coordination sites, thereby expanding the type of radionuclide that is useful in this invention (e.g., Indium and Yttrium)

As noted above, the sulfur atoms of the chelation compounds may bear sulfur protecting groups. Suitable sulfur protecting groups include any of the alkyl, acyl, and aryl groups, disulfides and bunte salts known by those of ordinary skill in the art. Preferred sulfur protecting groups are those that result in the formation of thioacetal, hemithioacetal, thioketal, hemithioketal, thioester or acetamidomethyl substituent. Particularly preferred groups include p-anisylidine, acetonyl, tetrahydrylfuranyl, ethoxyethyl, tetrahydrylpyranyl, acetamidomethyl and derivatives thereof. When conjugating a chelating compound of the present invention to a targeting moiety, the protecting groups may be removed just prior to metal complexation or during the radiolabeling reaction.

An acetamidomethyl sulfur-protecting group is represented by the following formula, wherein the sulfur atom shown is a sulfur donor atom of the chelating compound:

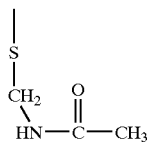

The acetamidomethyl group is displaced from the chelating compound during radiolabeling conducted at about 50° C. in a reaction mixture having a pH of about 3 to 6.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

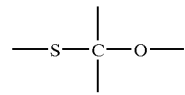

Preferred hemithioacetals generally are of the following formula, wherein the sulfur atom is a sulfur atom of the chelating compound, and a separate protecting group is attached to each of the sulfur atoms on the chelating compound:

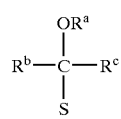

wherein $R^a$ is a lower alkyl group, preferably of from 2–5 carbon atoms, and $R^b$ is a lower alkyl group, preferably of from 1–3 carbon atoms Alternatively, $R^a$ and $R^b$ may be taken together with the carbon atom and the oxygen atom shown in the formula to define a nonaromatic ring, preferably comprising from 3–7 carbon atoms in addition to the carbon and oxygen atoms shown in the formula. $R^c$ represents hydrogen or a lower alkyl group wherein the alkyl group preferably is of from 1–3 carbon atoms Examples of such preferred hemithioacetals include, but are not limited to:

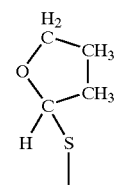

Tetrahydrofuranyl

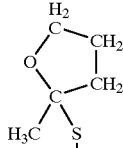

2-methyl tetrahydrofuranyl

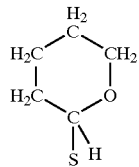

Tetrahydropyranyl

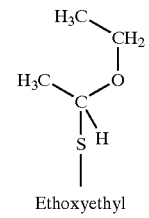

Ethoxyethyl

-continued

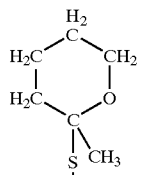

2-methyl tetrahydropyranyl

In one embodiment of the present invention, the sulfur protecting groups may join the two sulfur chelating atoms. Preferred embodiments of the sulfur protecting groups include thioketals and thioacetals, which may be prepared by condensation of the sulfur containing chelating compound with ketones and aldehydes, respectively. These particular sulfur protecting groups are represented by the following formula, wherein the sulfur atoms shown are the sulfur donor atom of the chelating compound:

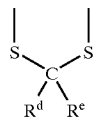

In the formula, $R^d$ and $R^e$ are independently selected from hydrogen, lower alkyl groups (preferably methyl or ethyl), lower alkoxy groups (preferably containing one or two carbon atoms), aryl groups, or taken together form a cyclic group (preferably a cyclopentane or cyclohexane ring).

These sulfur-protective groups are displaced during the radiolabeling reaction, conducted at acidic pH, in what is believed to be metal-assisted acid cleavage Covalent bonds form between the sulfur atoms and the metal radionuclide. A separate step for removal of the sulfur-protective groups is not necessary. The radiolabeling procedure thus is simplified. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. In general, such groups include esters, maleimides, and isothiocyanates, among others. Such groups may be present on the chelating compound as conjugation groups.

The aromatic ring atoms designated as X, Y, X' and Y' are independently selected from carbon, nitrogen, sulfur and oxygen to independently form five or six member rings, wherein the remaining ring atoms are carbon. The aromatic rings containing X and Y or X' and Y' are selected independently. For example, one ring may be a five member ring and the other a six member ring. For six member rings, where X, Y, X' and Y' are all carbon, the aromatic rings are benzene type rings. Where X, Y, X' and Y' are all nitrogen, the aromatic rings are pyrimidine type rings Where one of X or Y and one of X' or Y' are nitrogen, the aromatic rings are pyridine type rings.

For five member rings where X, Y, X' and Y' are all nitrogen, the aromatic rings are imidazole or pyrazole type rings. Where one of X or Y and one of X' or Y' are sulfur, the aromatic rings are thiophene type rings. Where one of X or Y and one of X' or Y' are sulfur and nitrogen, the aromatic rings are thiazole or isothiazole type rings, where on of X or Y and one of X' or Y' are oxygen, the aromatic rings are furan type rings, where one of X or Y and one of X' or Y' are oxygen and nitrogen, the aromatic rings are oxazole or isoxazole type rings.

Preferred embodiments of the aromatic rings designated X, Y, X' and Y' include benzene, pyrimidine, pyridine and thiophene, the most preferred being benzene or thiophene. These particular aromatic rings are interchangeable within the chelating compound formula because they are either structurally related or contribute similar properties, e.g., spatial configuration, electronic resonance and inductive properties (i.e., electron withdrawing and donating effects).

The chelation compounds and metal chelates of the present invention may also be asymmetric with respect to the nature of the aromatic rings. For example, the aromatic rings are a combination of benzene and pyridine types where X and Y are both carbon and either X' or Y' are both carbon, or either X or Y is nitrogen and X' and Y' is nitrogen, or either X or Y is nitrogen and X' and Y' are both carbon. In another embodiment, the aromatic rings are a combination of benzene and pyrimidine types where X and Y are both carbon and X' and Y' are both nitrogen, or X and Y are both nitrogen and X' and Y' are both carbon. In another embodiment, the aromatic rings are a combination of pyridine and pyrimidine types where either X or Y is nitrogen and X' and Y' are both nitrogen, or X and Y are both nitrogen and either X' or Y' are nitrogen. In another embodiment, the aromatic rings are a combination of benzene and thiophene types where either X or Y are both carbon and either X' or Y' is sulfur, or either X or Y is sulfur and X' and Y' are both carbon. In another embodiment, the aromatic rings are a combination of pyridine and thiophene types whether either X or Y is nitrogen and one of which is carbon and X' or Y' is sulfur and one of which is carbon, or either X or Y is sulfur, one of which is carbon and either X' or Y' is nitrogen, one of which is carbon. Further variations of the aromatic rings of the presently identified chelation compounds will be evident to one of ordinary skill in the based on the present disclosure in view of the art.

As noted above, in addition to providing chelation compounds, the present invention provides radionuclide metal chelate compounds wherein a metal is chelated (complexed) The chelation compounds of the present invention rapidly form stable metal complexes (radionuclide metal chelates) when reacted with a metal.

The preferred radionuclide metal chelate compound (complexes) of the present invention have the formula (II):

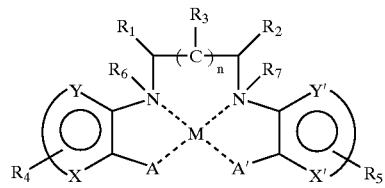

wherein $R_1$–$R_{11}$, n, X, X', Y, Y' are described above. A and A' may be independently selected from nitrogen, sulfur and oxygen. M is a radiometal or a radionuclide metal oxide or nitride, capable of being chelated by a compound of the present invention. Preferred metals and metal oxides or nitrides include radionuclides of copper, yttrium, ruthenium, technetium, rhodium, palladium, gadolinium, samarium, holmium, ytterbium, lutetium, indium, rhenium, gold, lead and bismuth. Particularly preferred are $^{64}$Cu, $^{67}$Cu, $^{90}$Y, $^{97}$Ru, $^{99m}$Tc, $^{105}$Rh, $^{109}$Pd, $^{111}$In, $^{153}$Sm, $^{159}$Gd, $^{166}$Ho, $^{175}$Yb, $^{177}$Lu, $^{186}$Re, $^{188}$Re, $^{198}$Au, $^{199}$Au, $^{203}$Pb, $^{212}$Pb and $^{212}$Bi.

Methods for preparing these isotopes are known Molybdenum/technetium generators for producing $^{99m}$Tc are commercially available. Procedures for producing $^{186}$Re include the procedures described by Deutsch et al. (*Nucl. Med. Biol.* 13(4):465–477, 1986) and Vanderheyden et al. (*Inorganic Chemistry* 24:1666–1673, 1985) (see also U.S. Pat. No. 5,053,186), and methods for production of $^{188}$Re have been described by Blachot et al. (*Intl. J. of Applied Radiation and Isotopes* 20:467–470, 1969) and by Klofutar et al. (*J. of Radioanalytical Chem.* 5:3–10, 1970) (see also U.S. Pat. No. 4,859,431). Production of $^{109}$Pd is described in Fawwaz et al. (*J. Nucl. Med.* 25:786, 1984). Production of $^{212}$Pb and $^{212}$Bi is described in Gansow et al. (*Amer. Chemi Soc. Symp. Ser* 241:215–217, 1984) and Kozah et al. (*Proc. Natl. Acad. Sci. USA* 83:474–478, 1986). Production of $^{90}$Y, a particle emitting therapeutic radionuclide resulting from transmutation processes (without non-radioactive carrier forms present), is commercially available from several sources, including Pacific Northwest National Laboratory, located in Richland, Wash.; Nordion International Inc., located in Kanata, Ontario, Canada and by Du Pont as NEN Research products located in North Billerica, Mass. Production of $^{153}$Sm is described in Goeckeler et al (*Nucl. Med. Biol*, Vol. 20, No. 5, pp. 657–661, 1993). $^{111}$In is commercially available as INDICLOR™ supplied by Amersham Healthcare located in Arlington Heights, Ill. $^{99m}$Tc is preferred for diagnostic use, and the other radionuclides listed above are preferred for therapeutic use.

In one embodiment of the present invention, chelation compounds of the invention including acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the chelation compounds of the invention.

In the case of technetium and rhenium being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}$TcO$_4^{-1}$ which is in the +7 oxidation level) or sodium perrhenate (i.e., $^{188}$ReO$_4^{-1}$, $^{186}$ReO$_4^{-1}$) may be combined simultaneously with a reducing agent and a chelating compound of the invention, in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including gluconic acid, glucoheptonic acid, tontanic acid, methylene disphosphonate, glyceric acid, glycolic acid, mannitol, oxalic acid, malonic acid, succinic acid, bicine, N,N'-bis(2-hydroxy ethyl) ethylene diamine, citric acid, ascorbic acid and gentisic acid. Good results are obtained using gluconic acid or glucoheptonic acid as the Tc-complexing agent and citric acid for rhenium. When the radionuclide in the form of such an exchange complex is reacted with the chelation compounds of the invention, the radionuclide will transfer to the chelation compounds, which bind the radionuclide more strongly to form chelates of the invention. In some instances, heating is necessary to promote transfer of the radionuclide. Radionuclides in the form of such complexes also are considered to be in "chelatable form" for the purposes of the present invention.

Y-90 is a particularly preferred radionuclide for therapy, because it exhibits favorable nuclear properties including high specific activity, long path length with respect to deposition of radiation in tissue, high equilibrium dose constant and favorable half-life properties. More specifically, the beta emission of Y-90 (Beta$_{av}$=0.937 MeV) makes it one of the most energetic of all beta emitters. The X$_{90}$ value of Y-90 is 5.34 mm (i.e., 90% of the energy emitted from a point source is absorbed in a sphere of 5.34 mm radius). Y-90 has a high equilibrium dose constant or mean energy/nuclear transition, Delta=1.99 Rad-gram/microcurie-hour, and a 64 hour half-life suitable for targeted therapy. Y-90 can be manufactured at high specific activity and is available as a generator product. Specific advantages of Y-90 are (1) that it has the capability to kill neighboring target cells not directly targeted by conventional methods (2) that more radiation is deposited per microcurie localized than for other beta emitters of lower mean particle energy (provided that a sufficiently large target volume is available).

Chelates of $^{212}$Pb, $^{212}$Bi, $^{109}$Pd, Cu$^{64}$ and Cu$^{67}$ may be prepared by combining the appropriate salt of the radionuclide with the chelating compound and incubating the reaction mixture at room temperature or at higher temperatures. It is not necessary to treat the lead, bismuth, palladium and copper radioisotopes with a reducing agent prior to chelation, as such isotopes are already in an oxidation state suitable for chelation (i.e., in chelatable form). The specific radiolabeling reaction conditions may vary somewhat according to the particular radionuclide and chelating compound involved.

In another embodiment of the present invention, where the sulfurs are protected by formation of a disulfide bond, chelation compounds of the invention are radiolabeled following reduction of the disulfide bond under mild conditions. For example, the disulfide may be reduced with SnCl$_2$ under conditions which do not reduce disulfides on proteins such as antibodies.

The chelation compounds and metal chelates of the present invention have a variety of uses, although certain uses are preferred depending upon the particular embodiment. In one embodiment of the present invention, the chelation compounds can be employed in the pretargeting methods as described in U.S. Pat. No. 5,608,060.

In another embodiment of the present invention, the chelation compounds and the radionuclide metal chelates are either reactive with a targeting moiety, or are conjugated to a targeting moiety. These compounds may be generally represented by the above-described compounds which bear the group Z. A chelating compound or a metal chelate that is reactive with a targeting moiety bears at least one conjugation group Z. Such conjugation groups include those described above (e.g., an active ester or a maleimide). Alternatively, the chelating compound or metal chelate may be conjugated to a targeting moiety Z. Such targeting moieties include those described above (e.g., proteins and antibodies). The preparation of representative chelation compounds that are reactive with targeting moieties is presented in the examples below. The preparation of representative radionuclide metal-targeting moiety conjugates is also presented in the examples below.

In the practice of the present invention, metal chelate-targeting moiety conjugates may be prepared by complexation of the radionuclide metal either before or after the chelating compound is conjugated to the targeting moiety. More specifically, a conjugate may be "pre-formed" or "post-formed," depending upon whether the chelating compound and targeting moiety are joined after or before the complexation of the radionuclide metal. A pre-formed conjugate comprises a chelating compound of the present invention that is first labeled with a radionuclide metal and then is conjugated to a targeting moiety. A post-formed conjugate comprises a chelating compound of the present invention that is first conjugated to a targeting moiety and then is labeled with a radionuclide metal. Thus, for pre-formed conjugates, the radionuclide is added to the chelating compound prior to the addition of the targeting moiety, whereas, for post-formed conjugates, the radionuclide is added after the addition of the targeting moiety. The final conjugate is the same regardless of how formed.

Generally, the chelation compounds of the present invention that are either reactive with targeting moieties or are conjugated to targeting moieties may be represented by the formula (I) above, where the specific embodiments of the elements of the formula include the following:

$R_1$ and $R_2$ may be independently hydrogen (H), an oxy group (=O); or —$(CH_2)_m$-Z where m is 0–10 and Z represents a conjugation group or targeting moiety; or $R_1$ and $R_2$ may be taken together to form a cyclic anhydride or a benzene ring.

The distance between the chelating nitrogen atoms of formula (I) may be varied by the imposition of a methylene group. When imposed, the methylene group may be substituted with $R_3$.

$R_3$ may be hydrogen, a lower alkyl group, an alkoxy group, a halogen, a hydroxyl group, a nitro group, or —$(CH_2)_m$-Z.

$R_4$ and $R_5$ may be attached at one or more of the aromatic ring positions, preferably the ring carbon atoms, and are independently selected from hydrogen, a lower alkyl group, an alkoxy group, a halogen, a hydroxyl group, a nitro group, and —$(CH_2)_m$-Z.

$R_6$ and $R_7$ are independently selected from lower alkyl, alkoxy, halogen, hydroxyl, nitro, —$(CH_2)_m$-Z, and

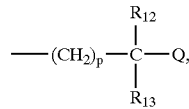

where Q represents multivalent acid functionality capable of coordinating with metal ions, and m=0 to 1; $R_{12}$ and $R_{13}$ are independently selected from hydrogen, hydroxyl, carboxyl, phosphonic, and hydrocarbon radicals having from 1–10 carbon atoms, and physiologically acceptable salts of the acid radicals, and $R_{12}$ and $R_{13}$ may be the same as or different from one another.

The chelation compounds reactive with or conjugated to targeting moieties have at least one Z, but may contain more than one Z. For example, any two groups selected from $R_1$–$R_5$ may be Z.

A, A', X, X', Y, Y' and n are as described above for formula (I).

Similarly, the radionuclide metal chelate compounds of the present invention that are either reactive with targeting moieties or are conjugated to targeting moieties may be represented by the formula (II). The specific embodiments of those elements of the formula denoted by $R_1$–$R_5$, n, X, X', Y, and Y' are as described immediately above for the chelation compounds. M is a radionuclide, radionuclide metal oxide or radionuclide metal nitride. The metal chelate compounds reactive with or conjugated to targeting moieties have at least one Z, but may contain more than one Z.

In a preferred embodiment, the compounds of the present invention are "$N_4$" ($N_4S_0O_0$) chelation compounds and metal chelates. Therefore, for preferred chelation compounds and metal chelates, A and A' are nitrogen. For particularly preferred chelation compounds, A and A' are nitrogen atoms joined together by a bond, i.e., $R_{10}$ and $R_{11}$ form T, the chelation compounds are tetraazacyclic, a tetradectane system. Preferred compounds of the present invention have X, Y, X' and Y' as carbon, nitrogen and sulfur. For the metal chelates of the present invention, technetium (e.g., $^{99m}Tc$) and indium (e.g., $^{111}In$) are the preferred metals for diagnostic purposes, and rhenium (e.g., $^{186}Re$ and $^{188}Re$) and yttrium (e.g., $^{90}Y$) are the preferred metals for therapeutic purposes.

Further, in a preferred embodiment, the compounds of the present invention, which are reactive with targeting moieties, possess a single conjugation group. A preferred conjugation group is the N-hydroxysuccinimide ester group.

In a preferred embodiment, in addition to the above-mentioned preferences, the conjugation group is an aromatic ring substituent, i.e., either $R_4$ or $R_5$ is —$(CH_2)_m$-Z. For one such preferred embodiment, n=1, $R_1$–$R_4$ are hydrogen, and $R_5$ is —$(CH_2)_m$-Z, where m=0 and Z is an active ester such as an N-hydroxysuccinimide ester. Alternatively, the conjugation group may be a substituent of the carbons linking the chelating nitrogens, i.e., $R_1$–$R_3$. In one such preferred embodiment, n=1, $R_1$ or $R_2$ are —$(CH_2)_m$-Z where m=0 and Z is an N-hydroxysuccinimide ester, $R_3$ is hydrogen, and $R_4$ and $R_5$ are hydrogen. In another such preferred embodiment, n=1, $R_1$ and $R_2$ are hydrogen, $R_3$ is —$(CH_2)_m$-Z as described immediately above, and $R_4$ and $R_5$ are hydrogen. $R_6$, $R_7$, $R_8$ and $R_9$ may be

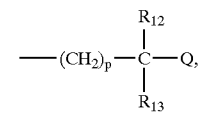

where Q represents multivalent acid functionality capable of coordinating with metal ions, and m=0 to 1; $R_{12}$ and $R_{13}$ are independently selected from hydrogen, hydroxyl, carboxyl, phosphonic, and hydrocarbon radicals having from 1–10 carbon atoms, and physiologically acceptable salts of the acid radicals, and $R_{12}$ and $R_{13}$ may be the same as or different from one another.

In another preferred embodiment, in the "$N_4$" ($N_4S_0O_0$) compounds of the present invention the conjugation group is an anhydride, i.e., $R_8$ and $R_{10}$ and $R_9$ and $R_{11}$ are taken together in a vicinyl configuration, to form a cyclic anhydride, —$(CH_2)_m$-Z where m=1 and Z is a carboxylic acid anhydride resulting from vicinyl dicarboxylic acids. In one such embodiment, in addition to the above-mentioned preferences, $R_1$–$R_5$ are hydrogen, n=1, $R_6$ and $R_7$ are

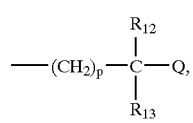

where Q represents multivalent acid functionality capable of coordinating with metal ions, and p=0 to 1; $R_{12}$ and $R_{13}$ are independently selected from hydrogen, hydroxyl, carboxyl, phosphonic, and hydrocarbon radicals having from 1–10 carbon atoms, and physiologically acceptable salts of the acid radicals, and $R_{12}$ and $R_{13}$ may be the same as or different from one another.

In another preferred embodiment, the conjugation group is an anhydride, i.e., $R_1$ and $R_2$ are taken together to form a cyclic anhydride. In one such embodiment, in addition to the above-mentioned preferences, $R_1$ and $R_2$ are taken together to form a cyclic anhydride, n=0, and $R_4$ and $R_5$ are fluorine.

For the compounds of the present invention which are conjugated to targeting moieties, preferred targeting moieties include proteins such as antibodies and annexin as well as binding proteins such as avidin and streptavidin.

In another aspect of the present invention, the chelation compounds and the radionuclide metal chelate compounds are used in radiopharmaceutical applications without the necessity for a conjugation group or targeting moiety. Such chelating and metal chelate compounds are useful by virtue of their lipophilic properties and may be generally represented by the above-described compounds which bear hydrolyzable group W.

Generally, the chelation compounds of the present invention that are useful without possessing a conjugating group or targeting moiety may be represented by the formula (I) above where the specific embodiments of the elements of the formula include the following.

$R_1$ and $R_2$ may be independently hydrogen (H), an oxy group (=O); or —$(CH_2)_m$—W where W represents a hydrolyzable group; or $R_1$ and $R_2$ may be taken together to form a cyclic anhydride or benzene ring.

The distance between the chelating nitrogen atoms of formula (I) may be varied the imposition of a methylene group, —$CH_2$. When imposed, the methylene group may be substituted with $R_3$.

$R_3$ may be hydrogen, a lower alkyl group, an alkoxy group, a halogen, a hydroxyl group, a nitro group, and —$(CH_2)_m$—W $R_4$ and $R_5$ may be attached at one or more of the aromatic ring positions, preferably the ring carbon atoms, and are independently selected from hydrogen, a lower alkyl group, an alkoxy group, a halogen, a hydroxyl group, a nitro group, or —$(CH_2)_m$—W.

The chelation compounds that are useful in the absence of a conjugation group of targeting moiety have at least one W, but may contain more than one W. For example, any two groups selected from $R_1$–$R_5$ may be W.

A, A', X, X', Y, Y', $R_6$, $R_7$, and $R_8$ through $R_{11}$ and n are as described above for formula (I).

Similarly, the radionuclide metal chelate compounds of the present invention that are useful without a conjugation group or targeting moiety may be represented by the formula (II) where the specific embodiments of the elements of the formula, $R_1$–$R_5$, $R_6$–$R_{11}$, n, X, X', Y and Y' are as described immediately above for the chelation compounds. M is a radionuclide, radionuclide metal oxide or radionuclide metal nitride. The metal chelates that are useful in the absence of a conjugation group or targeting moiety have at least one W, but may contain more than one W.

In a preferred embodiment, W is an enzyme hydrolyzable group, such as an ester or a carbamate Such groups are subject to hydrolysis by esterases commonly found in tissues such as the heart and bone marrow In a particularly preferred embodiment, the hydrolyzable group is an ethyl ester or ethyl carbamate.

Preferred embodiments of the compounds which possess hydrolyzable groups W include the preferences for M, A, A', X, Y, X' and Y' described above for the compounds which possess a conjugation group or a targeting moiety, Z. In a preferred embodiment, the compounds of the present invention having hydrolyzable groups W possess more than one W.

In one preferred embodiment, in addition to the above-mentioned preferences, the hydrolyzable group is an aromatic ring substituent, i.e., $R_4$ and $R_5$ are —$(CH_2)_m$—W. For one such embodiment, n=1, $R_1$–$R_3$ are hydrogen, and $R_4$ and $R_5$ are —$(CH_2)_m$—W, where m=0 and W is either an ester (i e., —$CO_2Et$), a carbamate (i.e., —NH—$CO_2Et$) or a nitrile (—CN) Alternatively, in another preferred embodiment, where both $R_4$ and $R_5$ are —$(CH_2)_m$—W as described immediately above, n=1, either $R_1$ or $R_2$ is an oxy group (=O) and $R_3$ is either hydrogen or —$(CH_2)_m$—W.

In another preferred embodiment, the hydrolyzable group W is a substituent of the carbon atoms linking the chelating nitrogens, i.e., one or more of $R_1$–$R_3$ is —$(CH_2)_m$—W. For example, in one such preferred embodiment, in addition to the above noted preference, n=0, $R_1$ and $R_2$ are —$(CH_2)_m$—W where m=0 and W is an ester, and $R_4$ and $R_5$ are fluorine. In another such preferred embodiment, n=1, either $R_1$ or $R_2$ is an oxy group (=O), $R_3$ is —$(CH_2)_m$—W as described immediately above, and $R_4$ and $R_5$ are methyl. In a further such preferred embodiment, n=1, $R_1$ and $R_2$ are hydrogen, $R_3$ is —$(CH_2)_m$—W as described above, and $R_4$ and $R_5$ are methoxy.

The lipophilic properties of these chelating and metal chelate compounds are due in part to the hydrophobic nature of hydrolyzable W. As noted above, W includes any neutral organic group that provides a charged group upon hydrolysis. Generally, the neutral organic group of W is hydrophobic and imparts lipophilic character to the chelating and metal chelate compounds.

The lipophilic compounds of the present invention are particularly useful in vivo where it is desirous to accumulate the metal chelates in tissues such as the heart and bone marrow. In such applications, the administered lipophilic metal chelates reach these tissues through the bloodstream and, because of their lipophilic properties, the metal chelates are absorbed by these tissues. Once absorbed into the tissues, the metal chelates are subject to hydrolysis where the hydrolyzable group, W (e.g., an ester), which imparted lipophilicity to the chelate is converted to a charged species (e.g., an acid if the ester is a carboxylate ester, and a base if the ester is a carbamate ester) and is thereby prevented from escaping the tissue.

Suitable hydrolyzable groups W included nitrites, carbamates, and esters. Preferred hydrolyzable groups include carbamates and carboxylate esters. Preferred carboxylate esters include methyl, ethyl, propyl and isopropyl esters. Preferred carbamate esters include methyl and ethyl esters.

The lipophilic metal chelates of the present invention, which bear hydrolyzable groups W, may undergo either chemical or enzymatic hydrolysis to yield residually charged metal chelates. To be effective, the metal chelates are resistant to rapid hydrolysis in the bloodstream, but are readily hydrolyzed upon uptake by the tissue of interest.

Hydrolysis which occurs in the bloodstream is primarily chemical in nature while tissue hydrolysis is primarily enzymatic.

In one embodiment, the compounds of the present invention are additionally resistant toward chemical hydrolysis. For example, the chelation compounds and metal chelates that bear ester groups, which are directly conjugated to the aromatic ring as either ortho or para substituents relative to the chelating nitrogen, are particularly stable toward chemical hydrolysis. Referring to the above formulas, these preferred compounds are represented by those compounds where $R_4$ and/or $R_5$ are —$(CH_2)_m$—W (m=0 and W is an ester), and where $R_4$ and/or $R_5$ is located ortho or para to the chelating nitrogen.

Such suitably substituted esters are resistant toward chemical hydrolysis by virtue of electron donation from the chelating nitrogen through the aromatic ring to the ester carbonyl group. This dispersal of electron density renders the ester carbonyl relatively electron rich and reduces its reactivity as an electrophile. Because the rate-determining step in ester hydrolysis is the addition of a nucleophilic water molecule to the ester carbonyl, ester carbonyl groups that are less electrophilic react more slowly toward nucleophilic addition. Thus, ester carbonyl groups which are stabilized toward nucleophilic addition by electron donating groups are resistant toward hydrolysis For these reasons, the above-described esters of the present invention are resistant toward chemical hydrolysis in the bloodstream.

While the efficacy of the administration of the lipophilic compounds of the present invention resides in part in their stability toward hydrolysis in the bloodstream, their ultimate utility as radiopharmaceutical agents relies on their capacity to be taken up and retained by various tissues. The uptake of these compounds into the tissue results from the particular character of the compounds and the permeability of the tissues toward such compounds.

The compounds of the present invention are retained within a tissue, such as malignant cells, by conversion of the lipophilic compounds to charged compounds (ionic species) by hydrolysis. The compounds of the present invention, which are resistant to chemical hydrolysis, are readily susceptible to enzymatic hydrolysis. Suitable hydrolyzable groups that are converted to charged compounds by enzymatic action include ester and carbamate groups which are converted to carboxylic acid and amino groups, respectively.

The compounds of the present invention may be taken up by various tissues, but are primarily intended for the tissues containing malignant cells and activated platelets. The metal chelates of the present invention may be selectively taken up by either malignant cell tissue depending upon the nature of the chelate.

The radiolabeled chelates of the present invention have use in diagnostic and therapeutic procedures, both for in vitro assays and for in vivo medical procedures. The radiolabeled chelates may be delivered (e.g., administered to a warm-blooded animal such as a human) intravenously, intraperitoneally, intralymphatically, locally, or by other suitable means, depending on such factors as the type of target site. The amount to be provided will vary according to such factors as the type of radionuclide (e.g., whether it is a diagnostic or therapeutic radionuclide), the route of delivery, the type of target site(s), the affinity of the targeting moiety, if employed, for the target site of interest, and any cross-reactivity of the targeting moiety, if employed, with normal tissues. Appropriate amounts may be established by conventional procedures, and a physician skilled in the field to which this invention pertains will be able to determine a suitable amount for a patient. A diagnostically effective dosage is generally from about 5 to about 35 and typically from about 10 to about 30 mCi per 70 kg body weight. A therapeutically effective dosage is generally from about 20 mCi to about 300 mCi or higher. For diagnosis, conventional non-invasive procedures (e.g., gamma cameras) are used to detect the biodistribution of the diagnostic radionuclide, thereby determining the presence or absences of the target sites of interest (e.g., tumors, heart, brain).

The comparatively low intestinal localization of the therapeutic radiolabeled chelates of the present invention or catabolites thereof permits increased dosages, since intestinal tissues are exposed to less radiation. The clarity and accuracy of diagnostic images also is improved by the reduced localization of radiolabeled chelates or catabolites thereof in normal tissues via an increase in target to non-target ratio.

The invention is further described through presentation of the following examples. These examples are offered by way of illustration and not by way of limitation.

EXAMPLES

Example I

N,N'-Bis(2-diaminophenyl)-1,3-propyldiamino hexaacetic acid 5

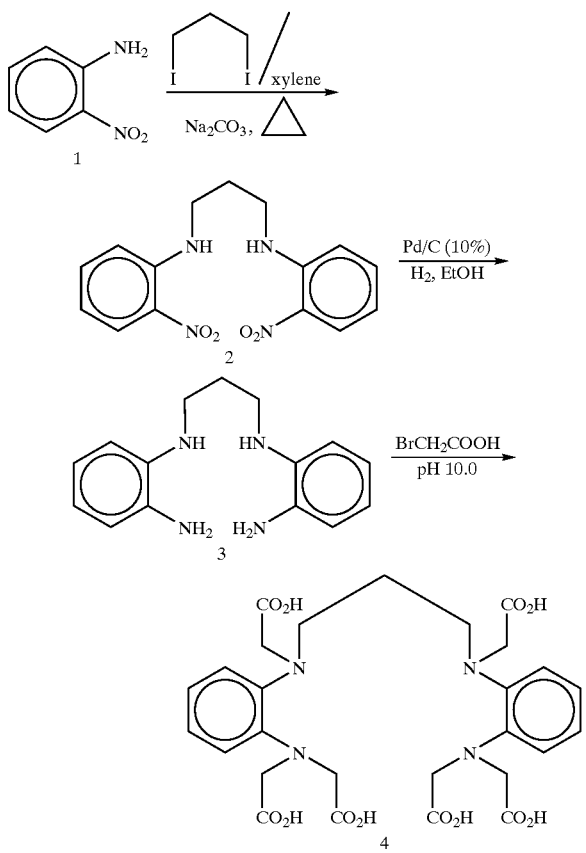

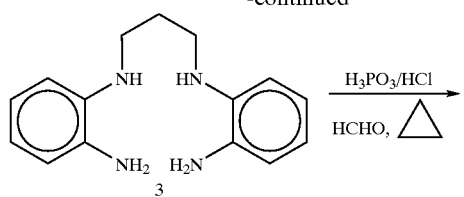

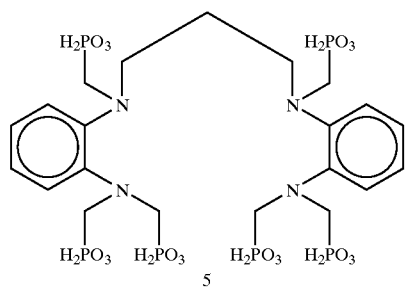

N,N'-Bis(2-dinitrophenyl)-1,3-propyldiamine 2

A stirred suspension of 30.0 g (0.217 mole) of 2-nitroaniline 1, 5.0 mL (0.044 mole) of 1,3-diiodopropane and 1.90 g (0.023 mole) of sodium bicarbonate in 100 mL xylene was heated at 140–145° C. for 36 hours. The reaction mixture was cooled down in an ice bath. The precipitate was collected by filtration. The red solid was washed several times with cold heptane to remove excess unreacted 2-nitroaniline 1 and 2-nitro N-methylaniline. The crude product was purified by flash chromatography on a silica gel column using 20% ethyl acetate in hexane as an elution solvent. After 2-nitro-aniline and 2-nitro N-methylaniline were removed from this solvent system, the desired product was then eluted from the column using 50% ethyl acetate in hexane. The fractions containing the product were combined. Solvent was removed under reduced pressure and dried to yield 10.30 g (15%) of compound 2.

N,N'-Bis(2-diaminophenyl)-1,3-propane-diamine 3

1.0 g (0.003 mole) of N,N'-Bis(2-dinitrophenyl)-1,3-propyldiamine 2 was taken into a parr hydrogenation bottle. 200 mL of 2% glacial acetic acid in absolute ethanol was added. To the suspension, 0.2 g of 10% palladium on activated carbon was added. The reaction mixture was catalytically reduced under hydrogen atmosphere at 40 PSI for 4–6 hours. The solution was filtered and the solvent was removed under reduced pressure and dried. The crude residue was placed in a sodium bicarbonate solution, and the free amine was extracted into methylene chloride three times, each time with 100 mL volume. The combined organic layer was dried over anhydrous sodium sulfate and filtered. Solvent was removed under reduced pressure and dried to yield crude residue The crude residue was purified by silica gel column chromatography using 50% ethyl acetate in hexane as an elution solvent The fractions containing the desired product were combined. Solvent was removed under reduced pressure and dried to yield 0.53 g (65%) of compound 3.

N,N'-Bis(2-diaminophenyl)-1,3-propane diaminohexacetic acid 4

To a stirred suspension of 5.0 g (0.020 mole) of N,N'-Bis(2-diaminophenyl)-1,3-propanediamine 3 in 75 mL of distilled water, 20.0 g (0.143 mole) of bromoacetic acid is added and magnetically stirred. The pH of the solution is adjusted to 10.0 with 2.0 N sodium hydroxide and the reaction mixture is heated in an oil bath at 45° C. for 16 hours The pH is maintained between 9.75 and 10.0 with 5.0 N sodium hydroxide during the entire course of reaction. The progress of the reaction is monitored by high performance liquid chromatography (HPLC) using PRP-X100 anion exchange column (supplied by Hamilton). Small amounts of bromoacetic acid (i.e., 100 to 200 mg) are added to the reaction mixture to drive the reaction to completion. The reaction mixture is diluted with sterile water to 2 liter volume and the pH is adjusted to 6.8 with 6.0 N hydrochloric acid. The conductivity for this solution is 4.89 ms/cm. It is further diluted to 4 liters with sterile water and the pH is adjusted to 8.2 with 2.0 N sodium hydroxide. The measured conductivity is 2.89 ms/cm. This solution is loaded on a 5×60 cm column with 900 mL bed volume of AG® 1-X2 (Bio-Rad Laboratories, Richmond, Calif.) (acetate form) resin which is prewashed with 1 liter 1.5 M acetic acid, 1.5 liter water, 0.5 liter 0.02 N ammonium acetate pH 7.18 and 4 liter water final eluent pH 4.28 by fast performance liquid chromatography (FPLC) at 40 mL/min. The column is eluted with water and gradually increased the solvent B (1.50 M acetic acid) of the gradient system. Fractions containing the product are pooled and solvent evaporated and dried under high vacuum to give 6.75 g (57%) of compound 4.

N,N'-Bis(2-diaminophenyl)-1,3-propane-diamino hexamethylene phosphonic acid 5

25.0 g (0.31 mole) of phosphorous acid and 25 mL of degassed water are taken into a 3 neck round bottom flask equipped with a dropping funnel, a thermometer and a magnetically stirring bar. The flask is flushed with nitrogen gas and a slow stream of nitrogen is maintained in the flask. Dissolution of the phosphorous acid is achieved upon stirring. 30 mL of concentrated hydrochloric acid is added to the reaction mixture and the stirring continued. The dropping funnel is charged with 20.0 g (0.078 mole) of N,N'-bis(2-diaminophenyl)-1,3-propanediamine dissolved in 25 mL water. The amine solution from the dropping funnel is added dropwise to the stirred acidic solution under nitrogen atmosphere After completion of addition, the reaction mixture is heated under reflux using an oil bath for at least 1.0 hour. Then the dropping funnel is charged with formaldehyde 27.2 g (0.938 mole) of a 37% aqueous solution and is added to the reaction mixture dropwise over a 2 to 3 hour time interval. The reaction mixture is continued heating under reflux throughout the entire formaldehyde solution addition period. After completion of all of the formaldehyde solution, the reaction mixture is continued stirring under reflux for an additional 3 to 4 hours. The reaction mixture is then allowed to cool and the product N,N'-Bis(2-diaminophenyl)-1,3-propane-diamino hexamethylene phosphonic acid is isolated from the reaction mixture and purified by ion exchange resin chromatography.

Example II 2,3,9,10-diphenylenyl-1,4,8,11-tetraazacyclo tetradecane-N,N',N",N'"-tetraacetic acid 7 and 2,3,9,10-diphenylenyl-1,4,8,11-tetraazacyclo tetradecane-N,N',N",N'"-tetramethylene phosphonic acid 8

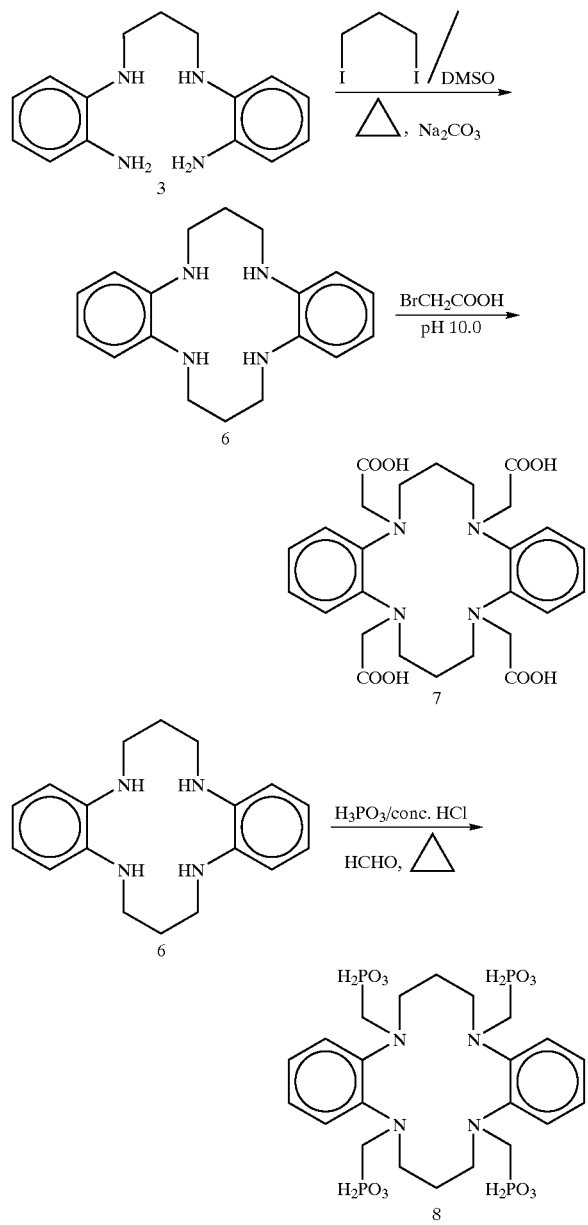

2,3,9,10-diphenylenyl-1,4,8,11-tetraazacyclo tetradecane 6

A stirred solution of 10.0 g (0.039 mole) of N,N'-Bis(2-diaminophenyl)-1,3-propane-diamine 3, 2.30 g (0.008 mole) of 1,3-diiodopropane and 6.50 g (0.08 mole) of sodium bicarbonate in 100 mL dry dimethyl sulfoxide is heated at 115° C. for 4 hours under nitrogen atmosphere. The dimethyl sulfoxide solvent is removed under high vacuum and dried. The crude product is extracted three times each time with 100 mL methylene chloride by partitioning with water. The combined methylene chloride layer is washed with brine and water. The organic layer is dried over anhydrous sodium sulfate and filtered. Solvent from the filtrate is removed under reduced pressure to yield crude product. The crude residue is purified by flash chromatography on silica gel column using 25% ethyl acetate in hexane as an elution solvent. The fractions containing the product are combined and the solvent removed under reduced pressure and dried to yield 1.20 g (10%) of compound 6.

2,3,9,10-diphenylenyl-1,4,8,11-tetraazacyclo tetradecane-N,N',N",N'"-tetraacetic acid 7:

To a stirred suspension of 10.0 g (0.034 mole) of 6 in 200 mL distilled water, 40.0 g (0.288 mole) of bromoacetic acid is added. The reaction mixture is stirred magnetically at room temperature. The pH of the solution is adjusted to 10.0 with 2.0 N sodium hydroxide and the reaction mixture is heated in an oil bath at 45° C. for 16 hours The pH is maintained between 9.75 and 10.0 with 5.0 N sodium hydroxide during the entire course of reaction. The progress of the reaction is monitored by HPLC using PRP-X100 anion exchange column and small amounts of bromoacetic acid is added to the reaction mixture to drive the reaction to completion. The reaction mixture is diluted with sterile water to 2 liter volume and the pH is adjusted to 6.8 with 6.0 N hydrochloric acid. The conductivity for this solution is 4.89 ms/cm. It is further diluted to 4 liters with sterile water and the pH is adjusted to 8.2 with 2.0 N sodium hydroxide. The measured conductivity is 2.89 ms/cm. This solution is loaded on 5×60 cm column with 900 mL bed volume of AG® 1-X2 (acetate form) resin which is prewashed with 1 liter 1.5 M acetic acid, 1.5 liter water, 0.5 liter 0.02 N ammonium acetate pH 7.18 and 4 liter water final eluent pH 4.28 by FPLC at 40 mL/min. The column is eluted with water and gradually increased the solvent B (1.50 M acetic acid) of the gradient system. Fractions containing the product are pooled and solvent evaporated and dried under high vacuum to give 7.10 g (40%) of compound 7.

2,3,9,10-diphenylenyl-1,4,8,11-tetraazacyclo tetradecane-N,N',N",N'"-tetramethylene phosphonic acid 8

5.0 g (0.061 mole) of phosphorous acid and 10 mL of degassed water are taken into a 3 neck round bottom flask equipped with a dropping funnel, a thermometer and a stir bar. The flask is flushed with nitrogen gas and a slow stream of nitrogen is maintained in the flask. Dissolution of the phosphorous acid is achieved upon stirring. 8.0 mL of concentrated hydrochloric acid is added to the reaction mixture and the stirring continued. The dropping funnel is charged with 4.0 g (0.014 mole) of 2,3,9,10-diphenylenyl-1,4,8,11-tetraazacyclo tetradecane, 6 dissolved in 10 mL water. The cyclic amine solution from the dropping funnel is added dropwise to the stirred acidic solution under nitrogen atmosphere After completion of addition, the reaction mixture is heated under reflux using an oil bath for at least 1 hour. Then the dropping funnel is charged with formaldehyde 5.0 g (0.172 mole) of a 37% aqueous solution and is added to the reaction mixture dropwise over a 2 to 3 hour time period. The reaction mixture is continued heating under reflux throughout the entire formaldehyde solution addition. After completion of all of the formaldehyde solution, the reaction mixture is continued stirring under reflux for an additional 3 to 4 hours. The reaction mixture is then allowed to cool and the product 2,3,9,10-diphenylenyl-1,4,8,11-tetraazacyclo tetradecane-N,N',N",N'"-tetramethylene phosphonic acid 8 is isolated from the reaction mixture and purified by ion exchange chromatography in 35% yield.

Example III 2,3,8,9,-diphenylenyl 5,6,11,12 -bis ortho carboxydiphenylenyl-1,4,7,10-tetraazacyclododecane N,N',N'',N'''-tetraacetic acid 13 and 2,3,8,9-diphenylenyl 5,6,11,12-bis ortho carboxydiphenylenyl-1,4,7,10-tetraazacyclododecane N,N',N'',N'''-tetramethylene Phosphonic Acid 14

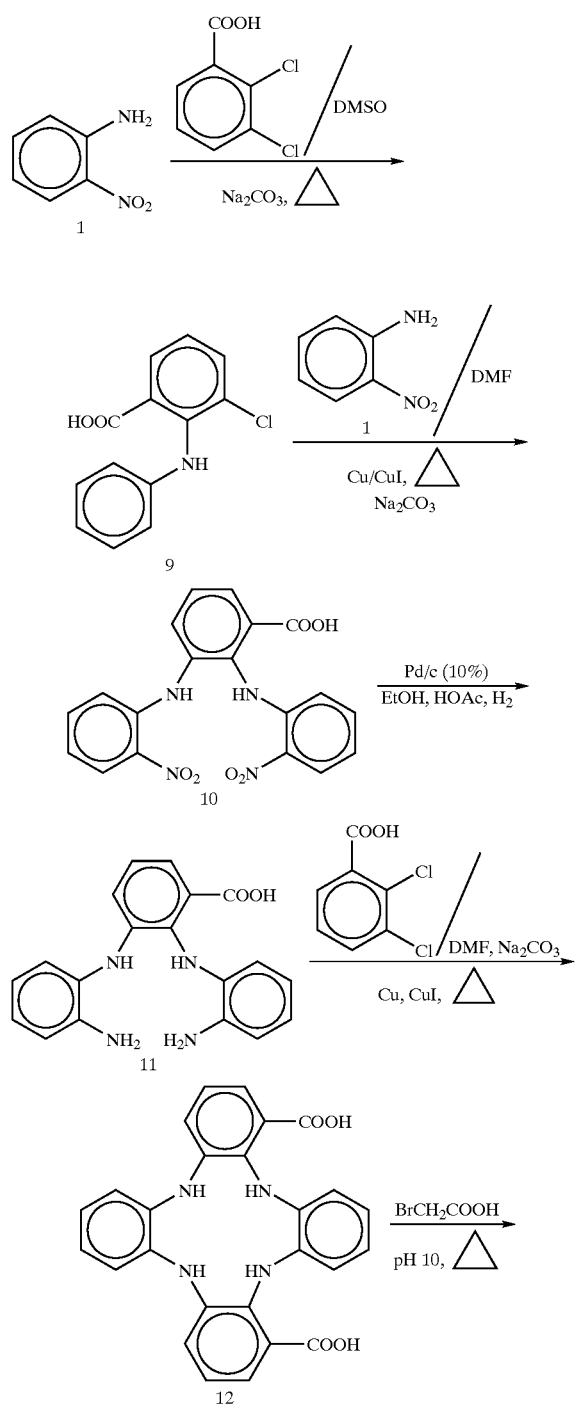
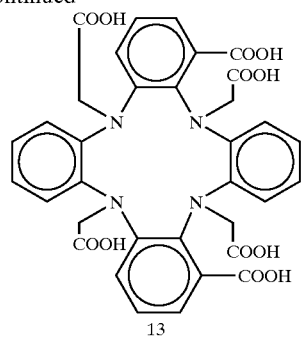
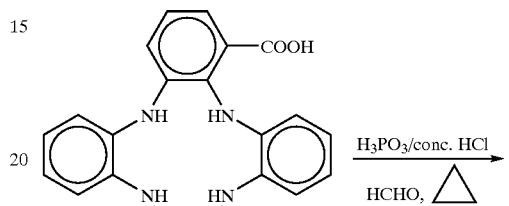
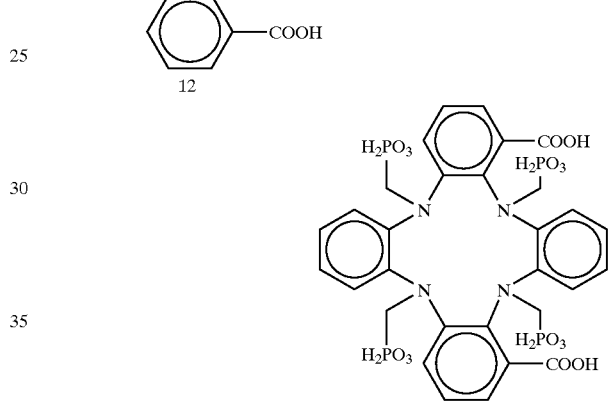

N-Phenyl N-(1-chloro 3-carboxyphenyl)amine 9

To a stirred solution of 20.0 g (0.145 mole) of 2-nitroaniline 1, 28.0 g (0.146 mole) of 2,3-dichlorobenzoic acid in 200 mL dry dimethyl sulfoxide, 20.0 g (0.19 mole) of anhydrous sodium carbonate is added. The reaction mixture is heated at 110° C. for 5 hours under nitrogen atmosphere. The dimethyl sulfoxide solvent from the reaction mixture is removed under high vacuum and dried. The crude product is extracted three times each time with 100 mL methylene chloride by partitioning into water. The combined methylene chloride layer is dried over anhydrous sodium sulfate and filtered. Solvent from the filtrate is removed under reduced pressure and dried. The crude residue is chromatographed on a silica gel 60 column (230–400 mesh) using 25% ethyl acetate in hexane as an elution solvent. The fractions containing the desired product are combined and the solvent removed under reduced pressure to yield 20.0 g (47%) of N-phenyl N-(1-chloro 3-carboxyphenyl) amine 9.

N,N'-Bis(2-dinitrophenyl)-2,3-diaminobenzoic acid 10

10.0 g (0.034 mole) of N-phenyl N-(1-chloro 3-carboxyphenyl) amine, 9 and 5.20 g (0.038 mole) of 2-nitro aniline 1 are dissolved in 200 mL anhydrous dimethylformamide (DMF) solvent. To the magnetically stirred solution, copper powder 0.22 g (0.0035 mole) and copper iodide 0.65 g (0.0034 mole) and sodium carbonate 3.62 g (0.034 mole) are added and heated under reflux in an oil bath. A slow stream of nitrogen gas is maintained throughout the course of the reaction. The reaction mixture is heated for 24 hours. Solvent from the reaction mixture is removed under high vacuum and dried. The crude residue is dissolved in water and extracted three times each time with 150 mL methylene chloride. The combined methylene chloride extracts is washed with brine and water. The organic layer is dried over anhydrous sodium sulfate and filtered. Solvent from the filtrate is removed under reduced pressure and dried. The crude residue is purified by silica gel column chromatography using 25% ethyl acetate in hexane as an elution solvent. Fractions containing the desired compound are pooled and the solvent removed under reduced pressure to yield 8.0 g (60%) of desired compound 10.

N,N'-Bis(2-diaminophenyl)-2,3-diaminobenzoic acid 11

2.0 g (0.00.5 mole) of N,N'-Bis(2-dinitrophenyl)-2,3-diaminobenzoic acid 10 is taken into a hydrogenation pressure bottle. 200 mL of 2% glacial acetic acid in absolute ethanol is added. To the suspension, 0.4 g of 10% palladium on activated carbon is added. The reaction mixture is catalytically reduced under hydrogen atmosphere using a parr hydrogenation apparatus at 60 PSI for 6 hours. The solution is filtered and the solvent removed under reduced pressure and dried. The crude residue is used as an acetate salt without further purification for the subsequent reactions. The yield of the product is 50–60%.

2,3,8,9-diphenylenyl 5,6,11,12-bis ortho carboxydiphenylenyl-1,4,7,10-tetraazadodecane 12

1.0 g (0.002 mole) of N,N'-Bis(2-diaminophenyl)-2,3-diaminobenzoic acid diacetate 11 and 0.47 (0.002 mole) of 2,3-dichloro benzoic acid are dissolved in 100 mL of anhydrous dimethylformamide solvent. To a magnetically stirred solution, copper powder 0.160 (0.1002 mole) and copper iodide 0.38 g (0.002 mole) and sodium carbonate 1.0 g (0.01 mole) are added and heated under reflux in an oil bath. A slow stream of nitrogen is maintained throughout the course of the reaction. The reaction mixture is heated at 115 to 120° C. for 36 hours. Solvent from the reaction mixture is removed under reduced pressure and dried The crude residue is purified by reverse phase HPLC using aqueous acetonitrile containing acetic acid as a mobile phase. The fractions containing the desired product are combined and the solvent removed under reduced pressure to give 50% of the desired compound, 2,3,8,9-diphenylenyl 5,6,11,12-bis ortho carboxy-diphenylenyl-1,4,7,10-tetraazadodecane 12.

2,3,8,9-diphenylenyl 5,6,11,12-bis ortho carboxydiphenylenyl-1,4,7,10-tetraazacyclododecane N,N',N'',N'''-tetraacetic acid 13

To a stirred suspension of 10.0 g (0.022 mole) 2,3,8,9-diphenylenyl 5,6,11,12-bis ortho carboxydiphenylenyl-1,4,7,10-tetraazacyclododecane 12 in 200 mL distilled water, 30.8 g (0.22 mole) of bromoacetic acid is added and magnetically stirred. The pH of the solution is adjusted to 10.0 with 2.0 N sodium hydroxide and the reaction mixture is heated in an oil bath at 45° C. for 20 hours. The pH of the reaction solution is maintained between 9.75 and 10.0 with 5.0 N sodium hydroxide during the entire course of reaction. The progress of the reaction is monitored by HPLC using PRP-X100 anion exchange column and small amounts of bromoacetic acid (i.e., 100 to 200 mg) are added to the reaction mixture to drive the reaction to completion. The reaction mixture is diluted with sterile water to a 2 liter volume and the pH is adjusted to 6.8 with 6.0 N hydrochloric acid. The conductivity for this solution is 4.89 ms/cm. It is further diluted to 4 liters with sterile water and the pH is adjusted to 8.2 with 2.0 N sodium hydroxide. The measured conductivity is 2.89 ms/cm. This solution is loaded on 5×60 cm column with 900 mL bed volume of AG® 1-X2 (acetate form) resin which is prewashed with 1 liter 1.5 M acetic acid, 1.5 liter water, 0.5 liter 0.02 N ammonium acetate pH 7.18 and 4 liter water final eluent pH 4.28 by FPLC at 40 mL/min. The column is eluted with water and solvent B (1.50 M acetic acid) of the gradient system is gradually increased. Fractions containing the product are pooled and solvent evaporated and dried under high vacuum to give 5.6 g (40%) of pure compound 13.

2,3,8,9-diphenylenyl 5,6,11,12-bis ortho carboxydiphenylenyl-1,4,7,10-tetraazacyclododecane N,N',N'',N'''-tetramethylene phosphonic acid 14

25.0 g (0.31 mole) of phosphorous acid and 20 mL of degassed water are taken into a 3 neck round bottom flask equipped with a dropping funnel, a thermometer, and a magnetic stir bar. The flask is flushed with nitrogen gas and a slow stream of nitrogen is maintained in the reaction flask. Dissolution of the phosphorous acid is achieved upon stirring. 15.0 mL of concentrated hydrochloric acid is added to the reaction mixture and the stirring continued. The dropping funnel is charged with 20.0 g (0.044 mole) of 2,3,8,9-diphenylenyl 5,6,11,12-bis ortho carboxydiphenylenyl 1,4,7,10-tetraazacyclododecane, 12 dissolved in 25 mL water. The cyclic tetramine solution from the dropping funnel is added dropwise to the stirred acidic solution under nitrogen atmosphere. After completion of addition, the reaction mixture is heated under reflux using an oil bath for at least 1.0 hour. The dropping funnel is charged with formaldehyde 27.2 g (0.938 mole) of a 37% aqueous solution and is added to the reaction mixture dropwise over a 2 to 3 hour time interval. The reaction mixture is continued heating under reflux throughout the entire formaldehyde solution addition period. After completion of all of the formaldehyde solution, the reaction mixture is continuously stirred under reflux for an additional 3 to 4 hours. The reaction solution is then allowed to cool and the product, 2,3,8,9-diphenylenyl-1,4,7,10-bis ortho-carboxydiphenylenyl-1,4,7,10-tetraazacyclododecane N,N',N'',N'''-tetramethylene phosphonic acid 14 is isolated from the reaction mixture and purified by ion exchange resin chromatography in 40–50% yield.

Example IV

N,N'-Bis(2-diaminophenyl)-1,3-propane N,N'-diacetic Acid 2,2'-tetraacetic acid dianhydride 15 Conjugated with Annexin V

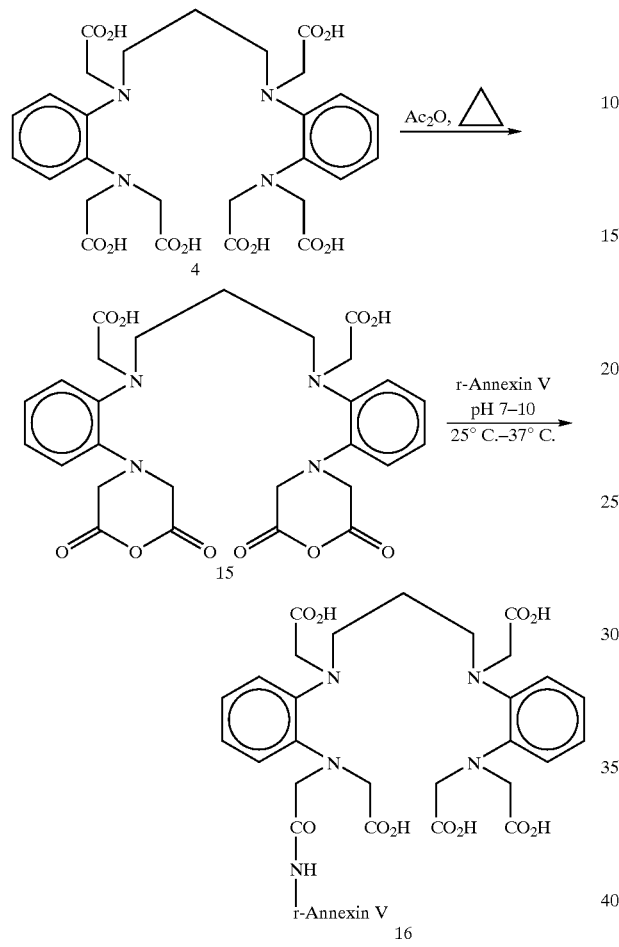

N,N'-Bis(2-diaminophenyl)-1,3-propane N,N'-diacetic Acid 2,2'-tetraacetic acid dianhydride 15

10.0 g (0.018 mole) of N,N'-Bis(2-diaminophenyl)-1,3-propanediamino hexaacetic acid 4 is placed in a 500 mL round bottom flask. To the flask is added 200 mL of acetic anhydride. The reaction mixture is stirred magnetically and heated under reflux for 48 hours. Solvent from the reaction mixture is removed under high vacuum and dried. The crude residue is purified by sublimation to yield 6.0 g (64%) of N,N'-Bis(2-diaminophenyl)-1,3-propane N,N'-diacetic acid 2,2'-tetraacetic acid dianhydride 15.

r-Annexin V Conjugation of N,N'-Bis(2-diaminophenyl)-1,3-propane N,N'-diacetic acid 2,2'-tetraacetic acid dianhydride 16

N,N'-Bis(2-diaminophenyl)-1,3-propane N,N'-diacetic acid 2,2'-tetraacetic acid dianhydride 15 precursor is offered to r-Annexin V in molar ratios of 300:1, 150:1, 75:1, 25:1, 10:1 and 5:1. Typically for a molar offering of 75:1 dianhydride to r-Annexin V ratio, 100 µl of dimethyl sulfoxide or DMF solvent containing 7.74 mg of $N_4$ ligand dianhydride is added dropwise with stirring to 2 mL of buffer with 25 mM HEPES ((N-[2-hydroxyethyl]piperazine-N'-[2-ethanesulfonic acid])), 150 mM sodium chloride, pH 8.0 containing 7.2 mg of r-Annexin V. The reaction mixture is stirred for 2 hours at 25° C.–37° C. followed by purification by PD-10 size exclusion chromatography equilibrated in PBS. The final product of the conjugate is exhaustively dialyzed in PBS.

Example V $Tc^{99m}$ radiolabeled N,N'-Bis(2-diaminophenyl)-1,3-propane N,N'-diacetic acid 2,2'-tetraacetic acid dianhydride 15

Example VI

Y90-Labeled N,N'-Bis(2-diaminophenyl)-1,3-propane diaminohexacetic acid 4 and N,N'-Bis(2-diaminophenyl)-1,3-propane-diamino hexamethylene phosphonic acid 5

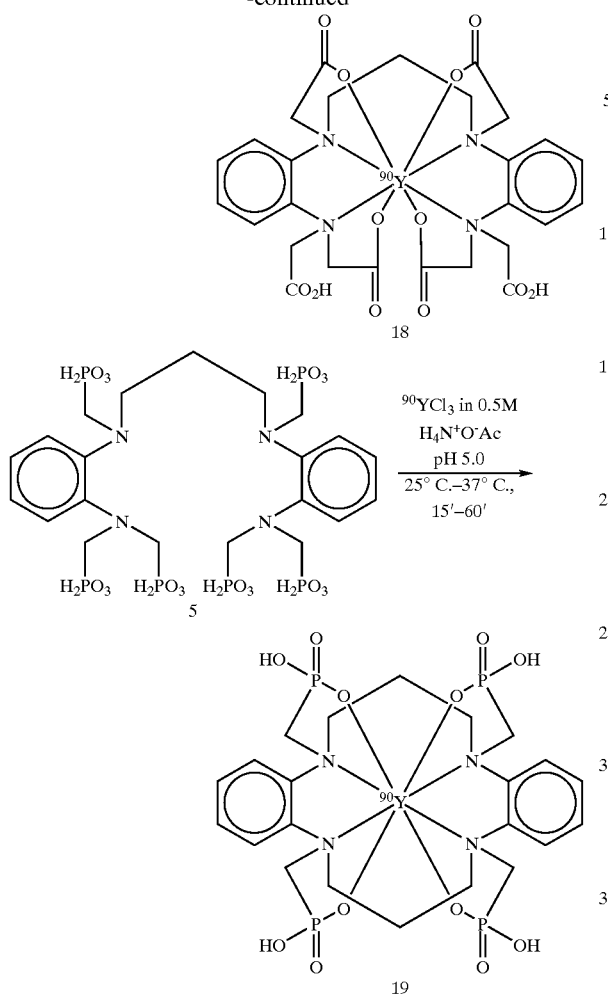

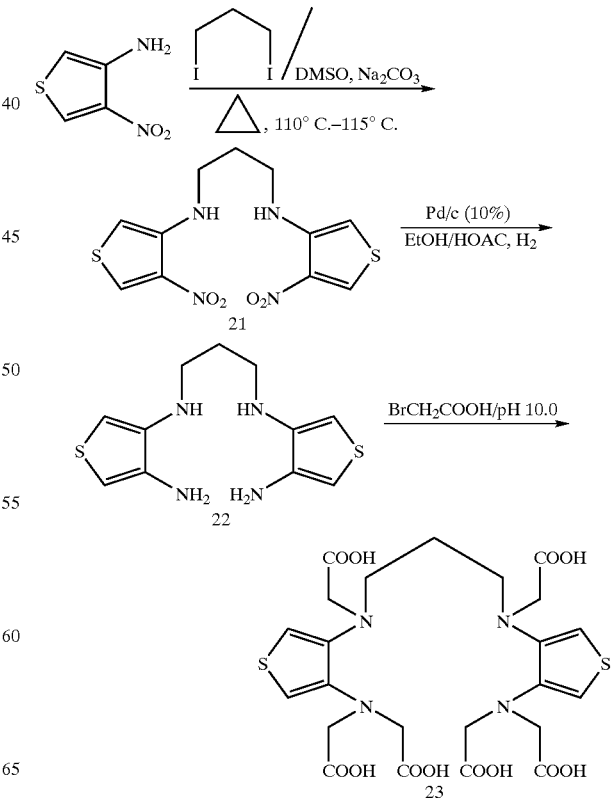

⁹⁹ᵐTc-radiolabeling Procedure for N₄ ligand-r-Annexin V Conjugate 16

Method A:

Stannous gluconate kits are prepared containing 5.0 mg sodium gluconate 100 micrograms stannous chloride, 1.0 mg (1 mg/ml) of N₄ ligand-r-Annexin V conjugate 16, and 0.1 to 1.0 mg of lactose. The pH is maintained between 5 and 7 using hydrochloric acid, acetic acid or sodium hydroxide. To the stannous gluconate kit is added 1.0 mL sodium pertechnetate (99mTcO⁻₄) with a specific activity of 50 mCi/mL The vial is thoroughly mixed and incubated at 25° C.-37° C. for 15'-30'. The percent formation of radiolabeled conjugate, remaining TcO₄, and hydrolyzed reduced technetium is determined by ITLC in 12% TCA as developing solvent.

Method B:

Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 5 and 7, preferably 6.0. To this stannous tartrate solution is added 1.0 mL of sodium pertechnetate at a specific concentration of 50 mCi/mL. The reaction mixture is allowed to stand at room temperature. In an evacuated vial, 200 μl of sodium phosphate (0.5 M, pH 8.0 or 10.0) and 1.0 mL of N,N'-Bis(2-diaminophenyl)-1,3-propanediamino hexaacetic acid, 4 (1.0 mg/mL) are added successively. Then Tc-99m-tartrate (50 mCi) is added, and the vial is incubated at 25° C.–37° C. for 15 '–30'. The percent formation of radiolabeled N₄ ligand, remaining TcO₄, and hydrolyzed reduced technetium is determined by ITLC in various solvents as developing solvent systems.

⁹⁰Y Radiolabeling of Compound 4 (18)

To carrier-free 0.6 mCi Y-90 Cl₃ (10 μl, 50 mM HCl, NEN Dupont), 0.18 mg of compound 4 in 450 μl of 2.0 M NH₄OAc, pH 5.0, is added and the reaction mixture is allowed to proceed for 30 minutes at 80° C. The percent of ⁹⁰Y radiolabeling monitored by gradient HPLC system equipped with a radiometric detector is greater than 99%.

⁹⁰Y Radiolabeling of Compound 5 (19)

To carrier free 0.6 mCi Y-90 Cl₃ (10 μl, 50 mM HCl, NEN Dupont), 18 mg of compound 5 in 450 μl of 2.0 M ammonium acetate, pH 7.0, is added and the reaction mixture is allowed to proceed for 30 minutes at 80° C. The percent of ⁹⁰Y radiolabeling as monitored by a gradient HPLC system equipped with a radiometric detection is greater than 99%.

Example VII

4-N,N'-Bis(3-diaminothiophenyl)-1,3-propanediamino hexaacetic acid 23 and 4-N,N'-Bis(3-diaminothiophenyl)-1,3-propanediamino hexamethylene phosphonic acid 24

-continued

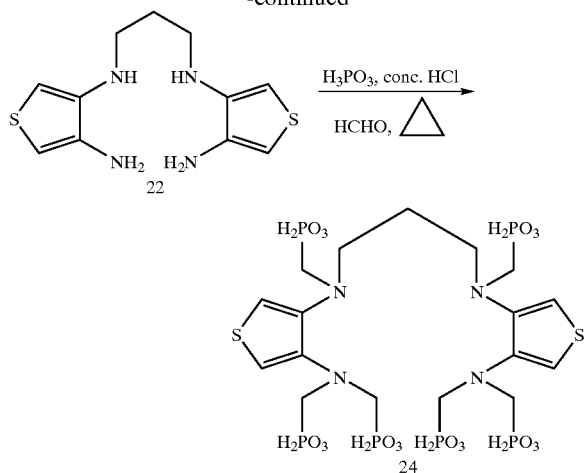

4-N,N'-Bis(3-dintirothiophenyl)-1,3-propyl diamine 21

To a stirred solution of 25.0 g (0.174 mole 3-nitro 4-aminothiophene and 10.2 g (0.034 mole) of 1,3-diiodopropane in 200 mL of dry dimethyl sulfoxide, 18.3 g (0.172 mole) of sodium carbonate is added and heated at 110° C.–115° C. for 12 hours. Solvent from the reaction mixture is removed under high vacuum and dried The crude residue is purified by silica gel column chromatography using 30% ethyl acetate in hexane as an elution solvent. Fractions containing the product are combined and solvent removed under reduced pressure to yield 8.0 g (14%) of compound 21.

4-N,N'-Bis(3-diaminothiophenyl)-1,3-propyldiamine 22

5.0 g (0.015 mole) of 4-N,N'-Bis(3-dinitrothiophenyl)-1,3-propyldiamine 21 is taken into a hydrogenation bottle. 250 mL of 2% glacial acetic acid in absolute ethanol is added. To the suspension, 0.5 g of 10% palladium on activated carbon is added. The reaction mixture is catalytically reduced under hydrogen atmosphere at 60 PSI for 4–6 hours in a parr hydrogenation apparatus. The solution is filtered and the solvent removed under reduced pressure and dried. The crude residue is taken into a saturated sodium bicarbonate solution and the free amine is extracted into methylene chloride three times each time with 150 mL volume. The combined organic layer is dried over anhydrous sodium sulfate and filtered. Solvent from the filtrate is removed under reduced pressure and dried to yield crude residue. The crude product is purified by silica gel column chromatography using 50% ethyl acetate in hexane as an elution solvent. Fractions containing the desired product are combined, solvent removed under reduced pressure and dried to yield 3.50 g (75%) of compound 22.

4-N,N'-Bis(3-diaminothiophenyl)-1,3-propanediamino hexaacetic acid 23

To a stirred suspension of 5.0 g (0.016 mole) of 4-N,N'-Bis(3-diaminothiophenyl)-1,3-propanediamine 22 in 100 mL of distilled water, 22.6 g (0.163 mole) of bromoacetic acid is added and magnetically stirred. The pH of the solution is adjusted to 10.0 with 2.0 N sodium hydroxide and the reaction mixture is heated in an oil bath at 45° C. for 16 hours The pH is maintained between 9.75 and 10.0 with 5.0 N sodium hydroxide during the entire course of reaction. Progress of the reaction is monitored by HPLC using PRP-X100 anion exchange column and small amounts of bromoacetic acid is added to the reaction mixture to drive the reaction to completion. The reaction mixture is diluted with sterile water to 2 liter volume and the pH is adjusted to 6.8 with 6.0 N hydrochloric acid. The conductivity for this solution is 4.89 Ms/cm. It is further diluted to 4 liters with sterile water and the pH is adjusted to 8.2 with 2.0 N sodium hydroxide. The measured conductivity is 2.89 Ms/cm. This solution is loaded on 5×60 cm column with 900 mL bed volume of AG® 1-X2 (acetate form) resin which is pre-washed with 1 liter 1.50 M acetic acid, 1.5 liter water, 0.5 liter 0.02 M ammonium acetate pH 7.18 and 4 liter water final eluent pH 4.28 by FPLC at 40 mL/min. The column is eluted with water and gradually increased the solvent B (1.50 M acetic acid) of the gradient system. Fractions containing the product are pooled, solvent evaporated and dried under high vacuum to give 7.50 g (81%) of compound 23.

4-N,N'-Bis (3-diaminothiophenyl) 1,3-propanediamino hexamethylene phosphonic acid 24

25.0 g (0.31 mole) of phosphorous acid and 25 mL of degassed water are taken into a 3 neck round bottom flask equipped with a dropping funnel, a thermometer and a magnetic stirring bar. The flask is flushed with nitrogen gas and a slow stream of nitrogen is maintained in the flask. dissolution of the phosphorous acid is achieved upon stirring. 30 mL of concentrated hydrochloric acid is added to the reaction mixture and stirring continued. The dropping funnel is charged with 20.0 g (0.065 mole) of 4-N,N'-Bis(3-diaminothiopheynl)-1,3-propanediamine dissolved in 25 mL of water. The amine solution from the dropping funnel is added dropwise to the magnetically stirred acidic solution under nitrogen atmosphere. After completion of addition the reaction mixture is heated under reflux using an oil bath for at least 1.0 hour. Then the dropping funnel is charged with formaldehyde 22.0 g (0.73 mole) of a 37% aqueous solution and is added to the reaction mixture dropwise over a 2–3 hour time interval. The reaction mixture is continued heating under reflux throughout the entire formaldehyde solution addition period. After completion of all of the formaldehyde solution, the reaction mixture is continued stirring under reflux for an additional 4–6 hours The reaction mixture is then allowed to cool and the product 4-N,N'-Bis(3-diaminothiophenyl)-1,3-propanediamino hexamethylene phosphonic acid 24 is isolated from the reaction mixture and purified by ion exchange resin chromatography.

Example VIII 2,3,9,10-[2,3-C, 9,10-C)-dithiophenyl]-1,4,8,11-tetraazacyclo tetradecane N,N',N'',N'''-tetraacetic acid 26 and 2,3,9,10-[2,3-C,9,10-C)-dithiophenyl]-1,4,8,11-tetraazacyclo tetradecane N,N',N'',N'''-tetramethylene phosphonic acid 27

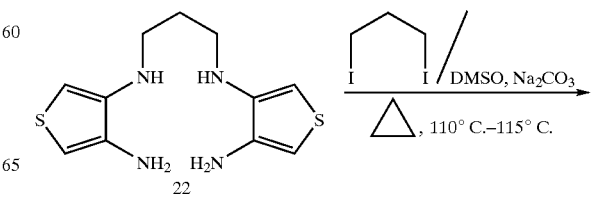

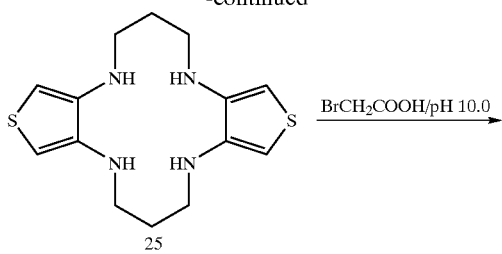

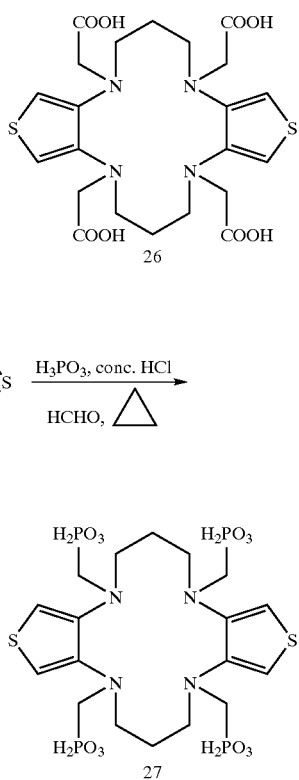

2,3,9,10-[(2,3-C'; 9,10-C')-dithiophenyl]-1,4,8,11-tetraazacyclo tetradecane 25

A stirred solution of 10.0 g (0.037 mole) of 4-N,N'-Bis (3-diaminothiophenyl)-1,3-propanediamine 22, 2.0 g (0.007 mole) of 1,3-diiodopropane and 5.70 g (0.068 mole) of sodium bicarbonate in 100 mL dry dimethyl sulfoxide is heated at 115° C. for 4 hours under nitrogen atmosphere. The dimethyl sulfoxide solvent is removed under high vacuum and dried. The crude product is extracted three times each time with 100 mL methylene chloride by partitioning with water. The combined methylene chloride layer is washed with brine and water. The organic layer is dried over anhydrous sodium sulfate and filtered. Solvent from the filtrate is removed under reduced pressure to yield crude residue. The crude residue is purified by flash chromatography on a silica gel column using 25% ethyl acetate in hexane as an elution solvent. The fractions containing the product are combined and the solvent removed under reduced pressure and dried to yield 4.0 g (35%) of compound 25.

2,3,9,10-[(2,3-C, 9,10-C)-dithiophenyl]-1,4,8,11-tetraazacyclo tetradecane N,N',N'',N'''-tetraacetic acid 26

To a stirred suspension of 10.0 g (0.033 mole) of compound 25 in 200 mL of distilled water, 40.0 g (0.288 mole) of bromoacetic acid is added. The reaction mixture is stirred magnetically at room temperature. The pH of the solution is adjusted to 10.0 with 2.0 N sodium hydroxide and the reaction mixture is heated in an oil bath at 45° C. for 20 hours. The pH is maintained between 9.75 and 10.0 with 5.0 N sodium hydroxide during the entire course of reaction. Progress of the reaction is monitored by HPLC using PRP-X100 anion exchange column and small amounts of bromoacetic acid (i.e., 100–200 mg) are added to the reaction mixture to drive the reaction to completion. The reaction mixture is diluted with sterile water to 2 liter volume and the pH is adjusted to 6.8 with 6.0 N hydrochloric acid The conductivity for this solution is 4.89 Ms/cm. It is further diluted to 4 liters with sterile water and the pH is adjusted to 8.2 with 2.0 N sodium hydroxide. The measured conductivity is 2.89 Ms/cm. This solution is loaded on 5×60 cm column with 900 mL bed volume of AG® 1-X2 (acetate form) resin which is prewashed with 1 liter 1.5 M acetic acid, 1.5 liter water, 0.5 liter 0.02 M ammonium acetate pH 7.18 and 4 liter water final eluent pH 4.28 by FPLC at 40 mL/min. The column is eluted with water and gradually increased the solvent B (1.50 M acetic acid) of the gradient system. Fractions containing the product are pooled and solvent evaporated and dried under high vacuum to give 8.0 g (46%) of compound 26.

2,3,9,10-[(2,3-C, 9,10-C)-dithiophenyl]-1,4,8,11-tetraazacyclo tetradecane N,N',N'',N'''-tetramethylene phosphonic acid 27

5.0 g (0.061 mole) of phosphorous acid and 10 mL of degassed water are taken into a 3 neck round bottom flask equipped with a dropping funnel, a thermometer and a stir bar. The flask is flushed with nitrogen gas and a slow stream of nitrogen is maintained in the flask. Dissolution of the phosphorous acid is achieved upon stirring. 10.0 mL of concentrated hydrochloric acid is added to the reaction mixture and the stirring continued. The dropping funnel is charged with 4.0 g (0.013 mole) of 2,3,9,10-[(2,3-C, 9,10-C)-dithiophenyl]-1,4,8,11-tetraazacyclo tetradecane 25 dissolved in 15 mL water. The cyclic amine solution from the dropping funnel is added dropwise to the stirred acidic solution under nitrogen atmosphere. After completion of addition, the reaction mixture is heated under reflux using an oil bath for at least 1.0 hour. Then the dropping funnel is charged with formaldehyde 5.0 g (0.172 mole) of a 37% aqueous solution and is added to the reaction mixture dropwise over a 2 to 3 hour time period. The reaction mixture is continued heating under reflux throughout the entire formaldehyde solution addition. After completion of all of the formaldehyde solution, the reaction mixture is continuously stirred under reflux for an additional 3 to 4 hours. The reaction mixture is then allowed to cool and the product 2,3,9,10-[(2,3-C; 9,10-C')-dithiophenyl]-1,4,8,11-tetraazacyclotetradecane N,N',N'',N'''-tetramethylenephosphonic acid 27 is isolated from the reaction mixture and purified by ion exchange chromatography in 25% yield.

Example IX

4-N,N'-Bis(3-diaminothiophenyl) 1,3-propanediamino hexamethylene phosphonic acid 24 and 2,3,9,10-[(2,3-C, 9,10-C)-dithiophenyl]-1,4,8,11-tetraazacyclo tetradecane N,N',N'',N'''-tetramethylene phosphonic acid 27 is $Y^{90}$ Labeled

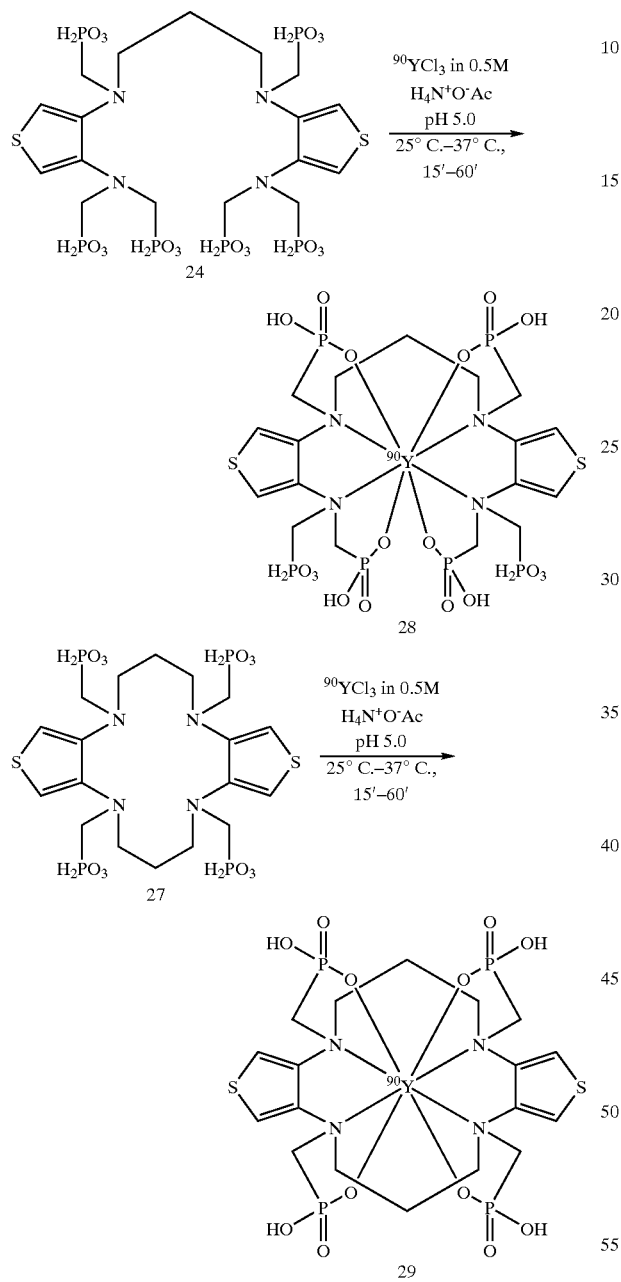

$^{90}$Y-Radiolabeling of Compound 24 (28)

To carrier free 0.6 mCi Y-90 Cl$_3$ (10 µl, 50 mM HCl, NEN Dupont), 0.18 mg of compound 24 in 450 µl of 2.0 M ammonium acetate, pH 5.0, is added and the reaction mixture is allowed to proceed for 30 minutes at 80° C. The percent of $^{90}$Y-radiolabeling monitored by a gradient HPLC system equipped with a radiometric detector is greater than 99%.

$^{90}$Y-Radiolabeling of Compound 27 (29)

To carrier free 0.6 mCi Y-90 Cl$_3$ (10 µl, 50 mM HCl, NEN Dupont), 180 mg of compound 27 in 450 µl of 2.0 M ammonium acetate, pH 7.0, is added and the reaction mixture is allowed to proceed for 30 minutes at 80° C. The percent of $^{90}$Y-radiolabeling monitored by gradient HPLC system equipped with a radiometric detection is greater than 99%.

Example X

Biocytin Conjugated on Tc$^{99m}$ Radiolabeled N,N'-Bis(2-diaminophenyl)-1,3-propane N,N'-diacetic Acid 2,2'-tetraacetic acid dianhydride 15

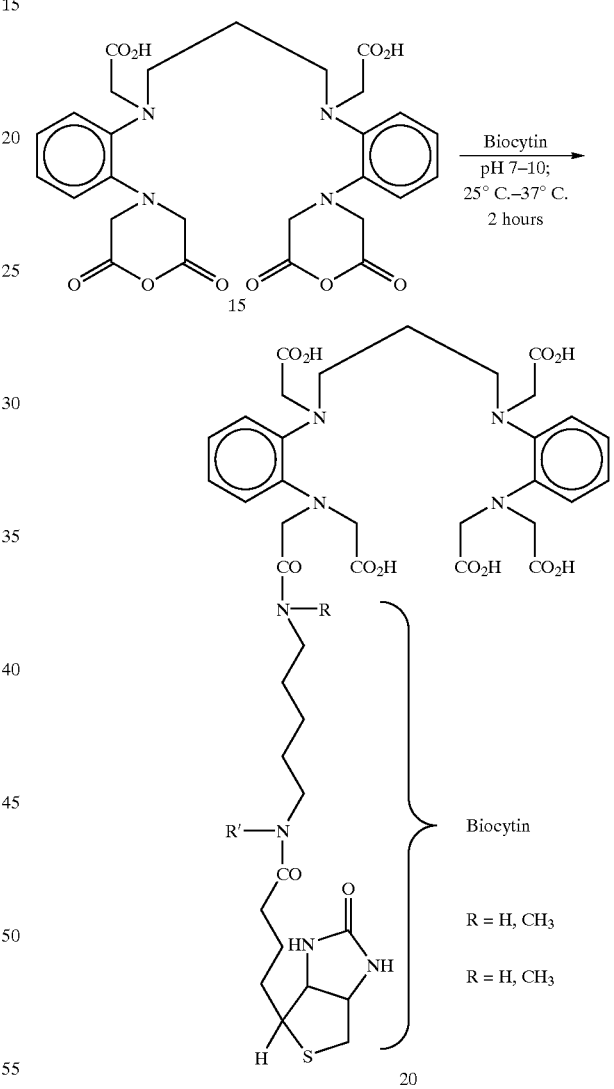

Biocytin Conjugation of N,N'-Bis(2-diaminophenyl)-1,3-propane N,N'-diacetic acid 2,2'-tetraacetic acid dianhydride 15 (20)

Typically to a stirred beaker of 25.0 mL of 0.20 M borate, pH 8.0, is added in sequential order 1.25 mL of dimethylformamide containing 129 mg (0.25 m moles) of N,N'-Bis(2-diaminophenyl)-1,3-propane N,N'-diacetic acid 2,2'-tetraacetic acid dianhydride chelate followed by 1.25 mL of DMF containing 9.3 mg (0.025 m moles) of biocytin free base. After incubation at 25° C. for 2 hours with stirring, the desired product is separated from the reactants and side products by preparative reverse phase C-18 chromatography, such as the DYNAMAX®-60A (supplied by Rainin Instrument Co.).

Alternatively in a stirred beaker of 25 mL of dimethylformamide is added 1.25 mL DMF containing 124 mg (0.25 m moles) of $N_4$-dianhydride chelate 15, 1.25 mL of DMF containing 9.3 mg (0.025 m moles) of biocytin free base and 1.25 mL of DMF containing 0.025 m moles of diisopropyl ethylamine. The reaction mixture is stirred at room temperature overnight. The desired product is purified by reverse phase C-18 chromatography.

The in vitro binding efficacy of the biocytin derivatized $N_4$ chelate to avidin or streptavidin is assessed using the standard HABA ([2(4'hydroxy-azobenzene)benzoic acid] dye) UV/VIS spectrophotometric assay of Green et al. (*Biochem. J.*, 94:23c–24c, 1965). The radiolabeling with radioactive metals $^{90}Y$ and $^{111}In$ is performed in 2.0 M acetate buffer, pH 5.0 as described earlier in labeling the $N_4$ tetramethylene phosphonate ligands.

Example XI

N,N'-Bis(2,disulfidyl-4-ethoxycarbonylphenyl)-1,3-propyldiamine

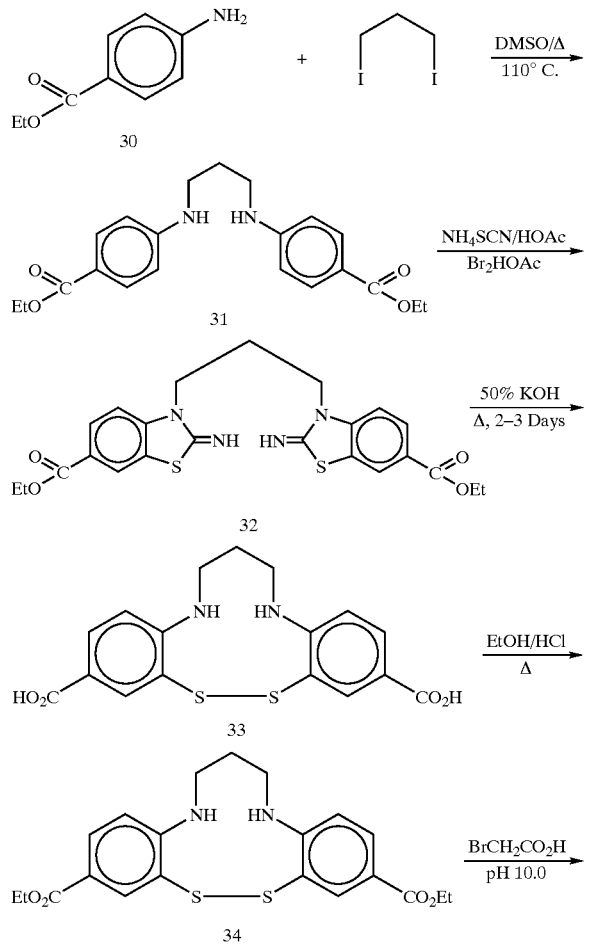

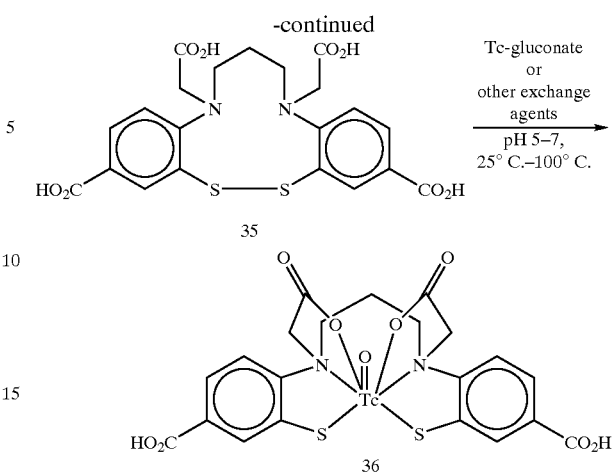

4,4-Diethoxycarbonylpropyl-1,3-dianiline 31

A stirred solution of 2.065 g (1.25 mole) ethyl-4-amino benzoate 3, 14.35 mL (0.125 mole) 1,3-diidopropane and 10.5 g (0.125 mole) sodium bicarbonate in 500 mL dry dimethyl sulfoxide was heated at 110° C. for 3 hours under nitrogen. Upon cooling, the mixture was poured into 2 L of ice water with stirring and the resulting precipitate collected by filtration. The precipitate was then washed with glacial acetic acid (14×75 mL) until all of the starting ethyl-4-aminobenzoate had been removed. After drying in vacuo, the product, 31, thus obtained was used in the next step without further purification.

1,3-di(2-imino-6-ethoxycarbonylbenzthiazolyl-3-)propane 32

Ammonium thiocyanate (16.5 g, 0.217 mole) was added to a magnetically stirred suspension of 4,4-diethoxycarbonylpropyl-1,3-dianiline (10.0 g, 0.027 mole) (prepared as described above) in 1500 mL glacial acetic acid. A solution of bromide (34.6 g, 0.216 mole) in 100 mL glacial acetic acid was then added dropwise to the suspension with stirring at room temperature. After stirring the reaction mixture overnight at room temperature, the dihydrobromide salt of the crude product was collected by filtration and dried. The product, 32, was isolated by dissolving the crude product in hot water, adjusting to basic pH with the addition of saturated sodium bicarbonate solution, collecting the precipitate by filtration, and drying in vacuo.

N,N'-Bis(2-disulfidyl-4-carbonylphenyl)-1,3-propyldiamine 33

Solid potassium hydroxide (20.0 g, 0.357 mole) was added to a suspension of the (1.0 g, 0.002 mole) 32 in 40 mL distilled water, and the resulting mixture was heated at 120° C. for 12 hours. Complete dissolution occurred after 1 hour. The reaction mixture was then cooled in an ice bath and the pH was adjusted to 5.0 with 5.0 N acetic acid. The aqueous solution was then extracted with three 100 mL portions of ethyl acetate The combined ethyl acetate extracts were dried over anhydrous sodium sulfate and the drying agent was filtered. Removal of solvent yielded the product 33.

N,N'-Bis(2-disulfidyl-4-ethoxycarbonylohenyl)-1,3-propyldiamine 34

A magnetically stirred suspension of 33 (0.5 g, 0.0013 mole) in 200 mL absolute ethyl alcohol was saturated with dry hydrogen chloride gas. The reaction mixture was then heated under reflux for 3 days. Upon cooling, the solvent was removed under reduced pressure, to yield the product, 34, as its dihydrochloride salt. A solution of the salt in 100 mL distilled water was adjusted to pH 8.5 to 9.0 with 0.2 M sodium bicarbonate solution and the aqueous solution was extracted with three 100 mL portion methylene chloride The combined methylene chloride extracts were dried over anhydrous sodium sulfate and the drying agent filtered Removal of the solvent under reduced pressure gave the crude product 34 which was isolated and purified by flash chromatography using silica gel and eluting with methylene chloride and ethyl acetate.

N,N'-Bis(2-disulfidyl-4-carboxyphenyl)-1,3-propyldiamine N,N'-diacetic acid 35

To a stirred suspension of 10.0 g (0.023 mole) of 34 in 200 mL distilled water, 40.0 g (0.288 mole) of bromoacetic acid is added. The reaction mixture is stirred magnetically at room temperature The pH of the solution is adjusted to 10.0 with 2.0 N sodium hydroxide and the reaction mixture is heated in an oil bath at 45° C. for 16 hours. The pH is maintained between 9.75 and 10.0 with 5.0 N sodium hydroxide during the entire course of reaction. The progress of the reaction is monitored by HPLC using PRP-X100 anion exchange column and small amounts of bromoacetic acid is added to the reaction mixture to drive the reaction to completion. The reaction mxiture is diluted with sterile water to 2 liter volume and the pH is adjusted to 6.8 with 6.0 N hydrochloric acid. The conductivity for this solution is 4.89 ms/cm. It is further diluted to 4 liters with sterile water and the pH is adjusted to 8.2 with 2.0 N sodium hydroxide. The measured conductivity is 2.89 ms/cm. This solution is loaded on 5×60 column with 900 mL bed volume of AG® 1-X2 (acetate form) resin which is prewashed with 1 liter 1.5 M acetic acid, 1.5 liter water, 0.5 liter 0.02 N ammonium acetate pH 7.18 and 4 liter water final eluent pH 4.28 by FPLC at 40 mL/min. The column is eluted with water and solvent B (1.50 M acetic acid) of the gradient system is gradually increased. Fractions containing the product are pooled and solvent evaporated and dried under high vacuum to give 7.10 g (40%) of compound 35.

Tc-99m Radiolabeling of N,N'-Bis(2-disulfidyl-4-carboxyphenyl)-1,3-propyldiamine N,N'-diacetic acid 36

A solution of 0.6 mL of 170 μg/mL N,Nμ-bis(2-disulfidyl-4-ethoxylcarbonylphenyl)-1,3-propyldiamine N,N'-diacetic acid in either acetonitrile or isopropanol is added to 1.1 mL of Tc-99m gluconate (prepared from 0.12 mg stannous chloride dihydrate, 5.0 mg sodium gluconate at pH 6.1–6.3, and 100 mCi/mL of Tc-99m pertechnetate). The resulting mixture is incubated either at room temperature for 15–30 minutes or heated at 75° C. for 2–5 minutes followed by cooling with an ice bath. The crude reaction mixture is then diluted with 3 mL water and purified by reverse phase chromatography. The crude product is loaded onto a pre-conditioned C-18 sample preparation cartridge (SPICE™ cartridge supplied by Analtech) and eluted with 5 mL water followed by 10 mL 5% ethanol-saline, and 10 mL 10% ethanol saline, respectively. The Tc-99m chelate product is eluted with 10 mL 50% ethanol-saline to give 75% radiochemical yield of the desired product. The radiochemical purity of the eluent is analyzed by reverse phase C-18 isocratic liquid chromatography using 50% ethanol-saline as the mobile phase at a flow rate of 0.8 mL per minute.

All publications and patent applications mentioned in this specification are herein incorporated by reference to the same extent, as if each individual publication or patent application is specifically and individually incorporated by reference From the foregoing, it will be appreciated that, although specific embodiments of the invention have been described herein for the purpose of illustration, various modifications may be made without deviating from the spirit and scope of the invention.

What is claimed is:

1. A complex of the formula:

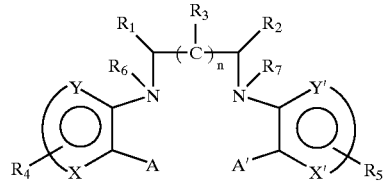

wherein:

M is a radionuclide metal or an oxide or nitride thereof:

n=0 or 1;

$R_1$ and $R_2$ are independently selected from hydrogen, =O, with the proviso that both are not =O, —$(CH_2)_m$-Z where m is 0–10 and Z represents a conjugation group or targeting moiety, and —$(CH_2)_m$—W where m is 0–10 and W represents a hydrolyzable group, or $R_1$ and $R_2$ are taken together to form a cyclic anhydride or a benzene ring;

$R_3$ is hydrogen, lower alkyl, alkoxy, halogen, hydroxyl, nitro, —$(CH_2)_m$-Z or —$(CH_2)_m$—W;

$R_4$ and $R_5$ are attached at one or more of the ring positions and are independently selected from hydrogen, lower alkyl, alkoxy, halogen, hydroxyl, nitro, —$(CH_2)_m$-Z and —$(CH_2)_m$—W;

$R_6$ and $R_7$ are independently selected from hydrogen with the proviso that both are not hydrogen, lower alkyl, alkoxy, halogen, hydroxyl, nitro, —$(CH_2)_m$-Z, —$(CH_2)_m$—W— and

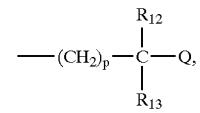

where Q represents a multivalent acid functionality group able to coordinate with metal ions, and p=0 to 1; $R_{12}$ and $R_{13}$ are independently selected from hydrogen, hydroxyl, carboxyl, phosphoric, and hydrocarbon radicals having from 1–10 carbon atoms, and physiologically acceptable salts of the acid radicals;

X, X', Y and Y' are carbon, to form member aromatic rings;

A and A' are oxygen, where an oxygen may bear a hydrogen; and the complex has at least one Z, W or Q.

2. A complex according to claim 1, wherein:

$R_1$ and $R_2$ are independently selected from hydrogen, =O, with the proviso that both are not =O, and —$(CH_2)_m$-Z where m is 0–10 and Z represents a conjugation group or targeting moiety, or $R_1$, and $R_2$ are taken together to form a cyclic anhydride or a benzene ring;

$R_3$ is hydrogen, lower alkyl, alkoxy, halogen, hydroxyl, nitro or —$(CH_2)_m$-Z;

$R_4$ and $R_5$ are attached at one or more of the ring positions and are independently selected from hydrogen, lower alkyl, alkoxy, halogen, hydroxyl, nitro and —$(CH_2)_m$-Z;

$R_6$ and $R_7$ are independently selected from hydrogen with the provision that both are not hydrogen, lower alkyl, alkoxy, halogen, hydroxyl, nitro and —$(CH_2)_m$-Z or

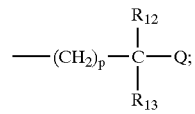

X, X', Y and Y' are defined as in claim 1;

A and A' are defined as in claim 1;

and said complex has at least one Z or Q.

3. A complex according to claim 2, wherein n=1; $R_1$, $R_2$, $R_3$ are hydrogen; $R_4$ and $R_5$ are independently selected from hydrogen and —$(CH_2)_m$-Z; $R_6$ and $R_7$ are

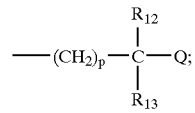

p=0, $R_{12}$ and $R_{13}$ are hydrogen, Q is a multivalent acid functionality capable of coordinating with metal ions; A and A' are defined as in claim 1.

4. A complex according to claim 2, wherein n=0; $R_1$ and $R_2$ are taken together to form a benzene ring; $R_4$ and $R_5$ are independently selected from hydrogen and —$(CH_2)_m$-Z; $R^6$ and $R^7$ are

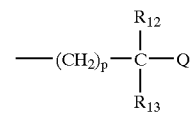

wherein Q is independently selected from a phosphonic acid and a carboxylic acid, p=0, and $R_{12}$ and $R_{13}$ are hydrogen.

5. A complex according to claim 2, wherein n=1; $R_1$, $R_2$ and $R_3$ are hydrogen; $R_4$, and $R_5$ are independently selected from hydrogen and —$(CH_2)_m$-Z; $R_6$ and $R_7$ are

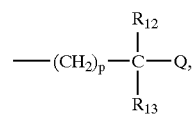

wherein Q is independently selected from a phosphonic acid and a carboxylic acid, p=0, and $R_{12}$ and $R_{13}$ are hydrogen;

with the proviso that said compound has at least one Z.

6. A complex according to claim 5, wherein Z is a targeting moiety selected from antibody fragments, biotin or annexin.

7. A complex according to claim 1, wherein:

$R_1$ and $R_2$ are independently selected from hydrogen, =O, with the proviso that both are not =O, and —$(CH_2)_m$—W where m is 0–10 and W represents a hydrolyzable group, or $R_1$ and $R_2$ are taken together to form a cyclic anhydride or a benzene ring;

$R_3$ is hydrogen, lower alkyl, alkoxy, halogen, hydroxyl, nitro or —$(CH_2)_m$—W;

$R_4$ and $R_5$ are attached at one or more of the ring positions and are independently selected from hydrogen, lower alkyl, alkoxy, halogen, hydroxyl, nitro and —$(CH_2)_m$—W;

$R_6$ and $R_7$ are independently selected from hydrogen, lower alkyl, alkoxy, halogen, hydroxyl, nitro, —$(CH_2)_m$—W and

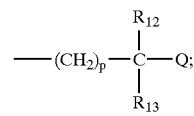

and said compound has at least one W.

8. A complex according to claim 7, wherein n=1; $R_1$, $R_2$ and $R_3$ are hydrogen; $R_4$ and $R_5$ are independently selected from hydrogen and —$(CH_2)_m$—W; $R_6$ and $R_7$ are

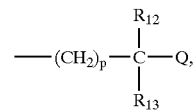

Q are independently selected from a phosphonic acid and a carboxylic acid, p=0, and $R_{12}$ and $R_{13}$ are hydrogen.

9. A complex of claim 8 wherein W is elected from the group consisting of ester, carbamate and nitrile.

10. A complex according to any one of claims 1–9, wherein the radionuclide is a radionuclide of technetium, copper, rhenium, lead, bismuth, ruthenium, rhodium, yttrium, samarium, holmium, indium, gold or palladium.

11. A complex according to claim 10, wherein the radionuclide is a radionuclide of technetium, rhenium, indium or yttrium.

12. A complex according to claim 10, wherein the radionuclide is a radionuclide of samarium.

13. A complex according to claim 10, wherein the radionuclide is a radionuclide of holmium.

* * * * *

UNITED STATES PATENT AND TRADEMARK OFFICE
CERTIFICATE OF CORRECTION

PATENT NO. : 6,936,700 B2
DATED : August 30, 2005
INVENTOR(S) : Sudhakar Kasina

It is certified that error appears in the above-identified patent and that said Letters Patent is hereby corrected as shown below:

Title page,
Item [56], References Cited, OTHER PUBLICATIONS,
"Francesconi et al.," reference, delete "methylproply" and insert -- methylpropyl --, therefor.
"Gürsu et al.," reference, delete "Instanbul" and insert -- Istanbul --, therefor.
"Jaffé," reference, delete "Rev.;" and insert -- Rev.: --, therefor.
"Léveillé et al.," reference, delete "Technetium 99m" and insert -- Technetium-99m --, therefor.
"Rajagopalan et al.," reference, delete "Tetradendate" and insert -- Tetradentate --, therefor.
"Schomäcker et al.," reference, delete "of" and insert -- on --, therefor.
"Tedjamulia et al.," reference, delete "1995" and insert --1985 --, therefor.

Column 2,
Line 16, delete "(Ch$_2$)" and insert -- (CH$_2$) --, therefor.

Column 3,
Line 15, after "above" insert -- . --.

Column 4,
Line 33, after "host" insert -- . --.
Line 36, delete "$^{99m}$TC" and insert -- $^{99m}$Tc --, therefor.

Column 5,
Line 11, after "use" insert -- . --.
Line 25, after "amides" insert -- . --.
Line 28, after "chelate" insert -- . --.
Line 30, after "chelation" insert -- . --.
Line 47, delete "i.e," and insert -- i.e., --, therefor.

Column 8,
Line 11, after "species" insert -- . --.
Line 45, delete "nitrites" and insert -- nitriles --, therefor.

Column 10,
Line 35, after "-(CH$_2$)$_m$-W" insert -- . --.

Column 11,
Line 13, after "sites" insert -- . --.
Line 31, after "Yttrium)" insert -- . --.

UNITED STATES PATENT AND TRADEMARK OFFICE
CERTIFICATE OF CORRECTION

PATENT NO. : 6,936,700 B2
DATED : August 30, 2005
INVENTOR(S) : Sudhakar Kasina

It is certified that error appears in the above-identified patent and that said Letters Patent is hereby corrected as shown below:

Column 12,
Lines 24 and 30, after "atoms" insert -- . --.

Lines 34-40, delete " 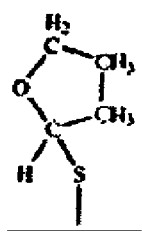 " and insert -- 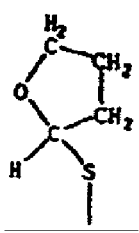 --, therefor.

Column 13,
Line 35, after "cleavage" insert -- . --.
Line 59, after "type rings" insert -- . --.

Column 14,
Line 41, after "(complexed)" insert -- . --.

Column 15,
Line 1, after "known" insert -- . --.
Line 13, delete "Chemi" and insert -- Chem. --, therefor.
Line 24, delete "Biol," and insert -- Biol., --, therefor.

Column 18,
Line 64, after "-(CH$_2$)$_m$-Z" insert -- , --.

Column 19,
Line 46, after "-(CH$_2$)$_m$-W" insert -- . --.

Column 20,
Line 2, after "carbamate" insert -- . --.
Line 4, after "marrow" insert -- . --.
Line 19, delete "(i e., -CO$_2$Et)" and insert -- (i.e., -CO$_2$Et) --, therefor.
Line 20, after "(-CN)" insert -- . --.
Line 20, delete "Alternatively, in another preferred" and insert the same as a new paragraph.
Line 56, delete "nitrites" and insert -- nitriles --, therefor.

Column 21,
Line 26, after "hydrolysis" insert -- . --.

UNITED STATES PATENT AND TRADEMARK OFFICE
CERTIFICATE OF CORRECTION

PATENT NO. : 6,936,700 B2
DATED : August 30, 2005
INVENTOR(S) : Sudhakar Kasina

It is certified that error appears in the above-identified patent and that said Letters Patent is hereby corrected as shown below:

Column 23,
Line 57, after "residue" insert -- . --.
Line 59, after "solvent" insert -- . --.

Column 24,
Line 5, after "hours" insert -- . --.
Line 53, after "sphere" insert -- . --.

Column 26,
Line 16, after "hours" insert -- . --.
Line 54, after "atmosphere" insert -- . --.

Column 29,
Line 52, after "dried" insert -- . --.

Column 35,
Line 29, after "dried" insert -- . --.
Line 67, after "hours" insert -- . --.

Column 36,
Line 45, after "hours" insert -- . --.
Lines 53 and 55, after "10-[" insert -- ( --.

Column 38,
Line 19, after "acid" insert -- . --.

Column 41,
Line 40, delete "Br$_2$HOAc" and insert -- Br$_2$/HOAc --.

Column 42,
Line 60, insert -- . -- before "The".
Line 64, delete "ethoxycarbonylohenyl" and insert -- ethoxycarbonylphenyl --, therefor.

Column 43,
Line 7, after "chloride" insert -- . --.
Line 9, after "filtered" insert -- . --.
Line 20, after "temperature" insert -- . --.
Line 28, delete "mxiture" and insert -- mixture --, therefor.

UNITED STATES PATENT AND TRADEMARK OFFICE
CERTIFICATE OF CORRECTION

PATENT NO. : 6,936,700 B2
DATED : August 30, 2005
INVENTOR(S) : Sudhakar Kasina

It is certified that error appears in the above-identified patent and that said Letters Patent is hereby corrected as shown below:

Column 44,
Line 5, after "reference" insert -- . --.

Lines 15-20, delete " 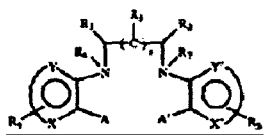 " and insert -- 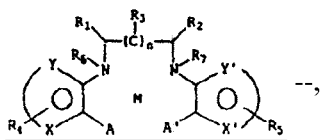 --, therefor.
Line 23, after "thereof" delete ":" and insert -- ; --, therefor.

Column 45,
Line 30, insert -- where -- before "p=0".
Lines 35-36, detete "$R^6$ and $R^7$" and insert -- $R_6$ and $R_7$ --, therefor.

Column 46,
Line 39, insert -- wherein -- before "Q".
Line 41, delete "elected" and insert -- selected --, therefor.

Signed and Sealed this

Twenty-ninth Day of November, 2005

JON W. DUDAS
*Director of the United States Patent and Trademark Office*